(12) United States Patent
Noll et al.

(10) Patent No.: US 8,080,418 B2
(45) Date of Patent: Dec. 20, 2011

(54) METHOD OF MAKING A THREE DIMENSIONAL CELL CULTURE MATRIX

(75) Inventors: Frederick E. Noll, Horseheads, NY (US); Wageesha Senaratne, Horseheads, NY (US); Ying Wei, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 957 days.

(21) Appl. No.: 12/075,093

(22) Filed: Mar. 7, 2008

(65) Prior Publication Data
US 2008/0220524 A1     Sep. 11, 2008

Related U.S. Application Data

(60) Provisional application No. 60/906,129, filed on Mar. 9, 2007.

(51) Int. Cl.
C12M 3/00      (2006.01)
(52) U.S. Cl. ...................... 435/395; 435/297.1
(58) Field of Classification Search .......... 435/395–397, 435/401, 402, 404
See application file for complete search history.

(56) References Cited

U.S. PATENT DOCUMENTS

| | | | |
|---|---|---|---|
| 4,458,678 A | 7/1984 | Yannas et al. | 128/155 |
| 4,711,780 A | 12/1987 | Fahim | 424/145 |
| 4,742,164 A | 5/1988 | Iguchi et al. | 536/56 |
| 5,116,747 A | 5/1992 | Moo-Young et al. | 435/178 |
| 5,264,359 A | 11/1993 | Enami et al. | 435/240.23 |
| 5,593,814 A | 1/1997 | Matsuda et al. | 430/320 |
| 5,620,706 A | 4/1997 | Dumitriu et al. | 424/485 |
| 5,834,274 A | 11/1998 | Hubbell et al. | 435/177 |
| 5,837,752 A | 11/1998 | Shastri et al. | 523/116 |
| 6,156,572 A | 12/2000 | Bellamkonda et al. | 435/395 |
| 6,334,968 B1 | 1/2002 | Shapiro et al. | 264/28 |
| 6,425,918 B1 | 7/2002 | Shapiro et al. | 623/11.11 |
| 6,642,050 B1 | 11/2003 | Goto et al. | 435/395 |
| 6,793,675 B2 | 9/2004 | Shapiro et al. | 623/11.11 |
| 6,838,449 B2 | 1/2005 | Asgharian | 514/54 |
| 6,896,894 B2 | 5/2005 | Brody et al. | 424/425 |
| 7,022,514 B2 | 4/2006 | Vodyanoy et al. | 435/260 |
| 7,033,603 B2 | 4/2006 | Nelson et al. | 424/426 |
| 7,125,960 B2 | 10/2006 | Keiichi | 530/350 |
| 7,189,526 B2 | 3/2007 | Kojima et al. | 435/30 |
| 7,267,982 B2 | 9/2007 | Tsuzuki et al. | 435/401 |
| 7,358,082 B2 | 4/2008 | Tsuzuki et al. | 435/293.1 |
| 2003/0073654 A1 | 4/2003 | Goffe et al. | 514/44 |
| 2003/0078672 A1 | 4/2003 | Shapiro et al. | 623/23.72 |
| 2004/0023924 A1 | 2/2004 | Lienart | 514/54 |
| 2004/0072338 A1 | 4/2004 | Tsuzuki et al. | 435/289.1 |
| 2004/0126405 A1 | 7/2004 | Sahatjian et al. | 424/423 |
| 2004/0143871 A1 | 7/2004 | Dhugga | 800/284 |
| 2005/0069572 A1 | 3/2005 | Williams et al. | 424/426 |
| 2005/0084512 A1 | 4/2005 | Denizeau et al. | 424/423 |
| 2005/0148922 A1 | 7/2005 | Reeves et al. | 602/52 |
| 2006/0154894 A1 | 7/2006 | Berry et al. | 514/54 |
| 2006/0172412 A1 | 8/2006 | Perrier et al. | 435/297.5 |
| 2006/0233765 A1 | 10/2006 | Messina et al. | 424/93.7 |
| 2006/0292690 A1 | 12/2006 | Liu et al. | 435/325 |
| 2007/0148770 A1 | 6/2007 | Jeong et al. | 435/325 |
| 2007/0280989 A1 | 12/2007 | Shahar et al. | 424/423 |

FOREIGN PATENT DOCUMENTS

| | | |
|---|---|---|
| EP | 0620844 B1 | 1/1996 |
| EP | 1 144 592 B1 | 1/2000 |
| EP | 1 123 975 A1 | 8/2001 |
| EP | 0901384 B1 | 9/2003 |
| GB | 2427411 A | 12/2006 |
| WO | 97/20937 | 6/1997 |
| WO | 98/54335 | 12/1998 |
| WO | 99/52356 | 10/1999 |
| WO | 00/49135 | 8/2000 |
| WO | 03/007873 | 1/2003 |
| WO | 2004/007683 | 1/2004 |
| WO | 2004/031371 A2 | 4/2004 |
| WO | 2004/060426 A1 | 7/2004 |
| WO | 2004060426 A1 | 7/2004 |
| WO | 2005/035735 A2 | 4/2005 |
| WO | 2005/041942 | 5/2005 |
| WO | 2005/089772 A2 | 9/2005 |
| WO | 2007/031871 A2 | 3/2007 |
| WO | 2007/047675 A2 | 4/2007 |
| WO | 2007/136227 | 11/2007 |

OTHER PUBLICATIONS

Tanaka et al., Formation of Locust Bean Gum Hydrogel by Freezing-Thawing 1998, Polymer International, 45: 118-126.*
Bucke, C., Immobilized Cells, Phil. Trans. R. Soc. Land. B300, 369-389 (1983).
Vinatier, C., et al., A silanized hydroxypropyl methylcellulose hydrogel for the three-dimensional culture of chondrocytes, Biomaterials 26 (2005) 6643-6651.
Goncalves, S., et al., Locust bean gum (LBG) as a gelling agent for plant tissue culture media, Scientia Horticulturae 106 (2005) 129-134.
Weigel PH., Rat hepatocytes bind to synthetic galactoside surface via a patch of asialoglycoprotein receptors, J Cell Biol 1980; 87: 855-61.
Kobayashi A, Akaike T, Kobayashi K, Sumitomo H., Enhanced adhesion and survival efficacy of liver cells in culture dishes coated with a lactose-carrying styrene homopolymer, Macromol. Chem. Rapid Commun. 1986; 7: 645-50.
Gutsche AY, Parsons-Wingerter P, Chand D, Saltzman WM, Leong KW., N-acetylglucosamine and adenosine derivatized surfaces for cell culture: 3T3 fibroblast and chicken hepatocyte response, Biotechnol. Bioeng., 1994; 43: 801-9.
Becton Dickinson Technical Bulletin #420, Effects of ECM on Cell Proliferation and Differentiation in Hepatocytes, 1997.

(Continued)

*Primary Examiner* — Ralph Gitomer
*Assistant Examiner* — Robert Yamasaki
(74) *Attorney, Agent, or Firm* — Susan S. Wilks

(57) ABSTRACT

This invention relates three dimensional porous cell culture matrices or scaffolds which have directional porous structure. More particularly, this invention relates to three dimensional porous cell culture matrices or scaffolds for cell culture which are derived from or contain gums including naturally occurring gums, plant gums, galactomannan gums or derivatives thereof. The invention also relates to methods of making the matrices, articles of manufacture (e.g., cell culture vessels and labware) having such matrices or scaffolds, methods of applying these materials to cell culture surfaces, and methods of using cell culture vessels having these three dimensional porous cell culture matrices or scaffolds.

7 Claims, 10 Drawing Sheets

OTHER PUBLICATIONS

Ying-Jie Wang, Hong-Ling Liu, Hai-Tao Guo, Hong-Wei Wen, Jun Liu, Primary hepatocyte culture in collagen gel mixture and collagen sandwich, World J Gastroenterol., 2004, 10(5), 699.

Yang J, Chung TW, Nagaoka M, Goto M, Cho CS, Akaike T. Hepatocyte-specific porous polymer-scaffolds of alginate/galactosylated chitosan sponge for liver-tissue engineering. Biotechnol. Lett., 2001; 23: 1385-9.

Dea, Iain C. M., Industrial polysaccharides, Pure & Appl. Chem., vol. 61, No. 7, pp. 1315-1322 (1989).

Park, In-Kyu, et al., Galactosylated chitosan as a synthetic extracellular matrix for hepatocytes attachment, Biomaterials 24 (2003) 2331-2337.

Nenoff, Tina M. et al., Membranes for Hydrogen Purification: An Important Step toward a Hydrogen-Based Economy, Mrs. Bulletin, vol. 31, Oct. 2006.

Weigel, Paul H., et al., Adhesion of Hepatocytes to Immobilized Sugars, The Journal of Biological Chemistry, vol. 254, No. 21, Issue of Nov. 10, pp. 10830-10838, 1979.

Edwards, Mary E., et al., The Seeds of Lotus japonicus Lines Transformed with Sense, Antisense, and Sense/Antisense Galactomannan Galactosyltransferase Constructs Have Structurally Altered Galactomannans in Their Endosperm Cell Walls, Plant Physiology, Mar. 2004, vol. 134, pp. 1153-1162.

Cho, C.S., et al., Galactose-carrying polymers as extracellular matrices for liver tissue engineering, Biomaterials 27 (2006) 576-585.

Gerecht-Nir, Sharon, et al., Three-Dimensional Porous Alginate Scaffolds Provide a Conducive Environment for Generation of Well-Vascularized Embryoid Bodies from Human Embryonic Stem Cells, Biotechnology and Engineering, vol. 88, No. 3, pp. 313-320, Nov. 5, 2004.

Pai, Vandita B., Khan, Saad A., Gelation and rheology of xanthan/enzyme-modified guar blends, Carbohydrate Polymers 49 (2002), 207-216.

Aydinli, Meltem, et al., Mechanical and Light Transmittance Properties of Locust Bean Gum Based Edible Films, Turk J. Chem 28 (2004) 163-171.

Jensen, Tor Wolf, et al, Polysaccharide Hydrogels as Variably Elastic Cell Culture Substrates, http://aiche.confex.com/aiche/2006/techprogram/P69213.HTM.

Yang J, Goto M, Ise H, Cho CS, Akaike T., Galactosylated alginate as a scaffold for hepatocytes entrapment, Biomaterials 2002; 23: 471-9.

Chung TW, Yang J, Akaike T, Cho KY, Nah JW, Kim SI, et al., Preparation of alginate/galactosylated chitosan scaffold for hepatocyte attachment, Biomaterials 2002; 23: 2827-34.

Seo SJ, Akaike T, Choi YJ, Shirakawa M, Kang IK, Cho CS., Alginate microcapsules prepared with xyloglucan as a synthetic extracellular matrix for hepatocyte attachment, Biomaterials 2005; 26:3607-15.

Emmanouhl S. Tzanakakis, Linda K. Hansen and Wei-shou Hu, The role of Actin Filaments and Microtubules in Hepatocyte Spheroid Self-Assembly, Cell Motility and the Cytoskeleton 48:175-189 (2001).

Seo, Seog-Jin, et al., Xyloglucan as a synthetic extracellular matrix for hepatocyte attachment, J. Biomater. Sci. Polymer Edn, vol. 15, No. 11, pp. 1375-1387 (2004).

de Lima, D.U., Buckeridge, M.S., Interaction between cellulose and storage xyloglucans: the influence of the degree of galactosylation, Carbohydrate Polymers 46 (2001) 157-163.

Yakagaku, Artificial Glycoconjugate Polymers Biofunctional Materials Having Carbohydrates as Recognition Signals, Journal of Japan Oil Chemists' Society, vol. 43, 1994, 960-967.

* cited by examiner

METHOD OF MAKING A THREE DIMENSIONAL CELL CULTURE MATRIX

CROSS-REFERENCE TO RELATED APPLICATIONS

This Application claims the benefit of U.S. Provisional Application Ser. No. 60/906,129 filed Mar. 9, 2007 and entitled "Coatings for Cell Culture Surfaces" which is incorporated by reference herein. This Application is related to application Ser. No. 12/075,079 filed on Mar. 7, 2008 and entitled "Gum Coatings for Cell Culture, Methods of Manufacture and Methods of Use."

FIELD THE INVENTION

This invention relates to cell culture surfaces and matrices. More particularly, this invention relates to cell culture surfaces and matrices which are derived from or contain gums including naturally occurring gums, plant gums, galactomannan gums or derivatives thereof. Even more particularly, the invention relates to naturally occurring gums which are processed to produce three dimensional directional porous matrices for cell culture. The invention also relates to articles of manufacture (e.g., cell culture vessels and labware) having such matrices, methods of making and providing the matrices to cell culture surfaces, and methods of using cell culture vessels having such matrices.

BACKGROUND OF THE INVENTION

In vitro culturing of cells provides material necessary for cell biology research, and provides much of the basis for advances in the fields of pharmacology, physiology and toxicology. However, isolated cultured eukaryotic cells living in an incubator in a culture vessel bathed in cell culture media often have very different characteristics compared to individual cells in vivo. Information obtained from experiments conducted on primary and secondary cultures of eukaryotic cells is informative to pharmacologists, physiologists and toxicologists only to the extent that cultured cells have the same characteristics as intact cells.

Eukaryotic cells can grow on surfaces of cell culture vessels. For example, cells in liquid media can be introduced into a cell culture vessel such as a cell culture flask or a multi-well cell culture plate, the cell culture vessel placed into a suitable environment such as an incubator, and the cells allowed to settle onto a surface of the cell culture vessel where they attach, grow, and divide. However, some cells perform better than others when growing on a flat surface. Some cells require different surfaces in order to maintain a more natural phenotype, and to provide optimal in vitro data.

SUMMARY

The present invention relates to a three dimensional porous cell culture matrix made from at least one gum material, including naturally occurring gums, plant gums, galactomannan gums or derivatives thereof. In an embodiment, the invention relates to a three dimensional porous cell culture matrix or scaffold made from at least one galactomannan gum. Galactomannan gums include locust bean gum, (also known as carob bean gum, carob seed gum, carob gum), guar gum, *cassia* gum, tara gum, mesquite gum, and fenugreek gum. In embodiments, the galactomannan gum may have a mannose/galactose ratio of from 1:1 to 5:1 or 10:1. In embodiments, the three dimensional matrix may be directional. That is, the porous structures of the three dimensional porous matrix may be directed in the manufacturing process to form pores that run in one direction or multiple directions. In embodiments, the gum material can be processed, purified, chemically modified, treated, subjected to heating or freeze-thaw cycles, mixed with other gums or with other materials such as biologically active materials, charged, hardened, softened or otherwise chemically or physically modified or otherwise modified, "tuned" or "tunable" to suit the needs of a particular cell culture. In embodiments, the gum matrix can be dry, wet, in the form of a gel, a hydrogel, affixed to a cell culture surface or free-floating in culture.

In yet another embodiment, the three dimensional porous cell culture matrix of the present invention may be manufactured in a larger format, and cut from the larger format to fit within the dimensions of a cell culture vessel or well. In additional embodiments, the three dimensional porous cell culture matrix may be affixed or pinned to a cell culture surface by means of a pinning device which may be a snap ring or hooks molded into the cell culture vessel substrate, or by any other method. Or, in alternative embodiments, the three dimensional porous cell culture matrix of the present invention may float free in culture.

In an embodiment, the present invention also includes a cell culture vessel for eukaryotic cell culture comprising a substrate and a three dimensional porous cell culture matrix wherein the matrix comprises at least one galactomannose gum. In an embodiment of the present invention, the cell culture vessel can be plastic or glass. In a further embodiment of the present invention, the cell culture vessel can be labware.

In yet another embodiment, the present invention also includes a method of making a cell culture vessel with the steps of preparing a solution, introducing the solution to a container, applying a heat sink to the container and freezing the solution in the container to form a three dimensional porous cell culture matrix. The three dimensional porous cell culture matrix may have directional porous structure. In additional embodiments, the present invention includes methods of culturing cells including the steps of introducing cells to a cell culture vessel containing a three dimensional porous cell culture matrix, adding cell culture media, and incubating the cells, which may be hepatocytes, in the cell culture vessel.

BRIEF DESCRIPTION OF THE DRAWINGS

The invention is best understood from the following detailed description when read with the accompanying figures.

DETAILED DESCRIPTION

Figure 1:
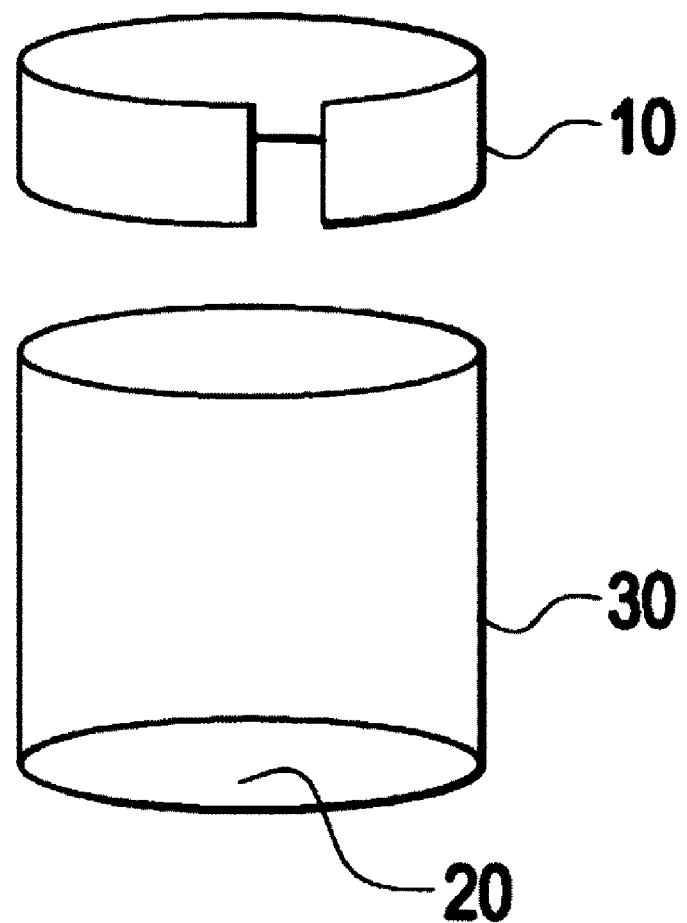
FIG. 1 illustrates an embodiment of a pinning device of the present invention.

Embodiments of the present invention provide cell culture matrices which provide a cell culture environment that is favorable for cell growth in vitro. In embodiments, the present invention provides three-dimensional porous cell culture matrices or scaffolds made from naturally occurring branched galactose based polysaccharides. These naturally occurring branched galactose based polysaccharides include locust bean gum (also known as carob bean gum, carob seed gum, carob gum), guar gum, *cassia* gum, tragacanth gum, tara gum, karaya gum, gum acacia (gum Arabic), ghatti gum, cherry gum, apricot gum, tamarind gum, mesquite gum, larch gum, psyllium, fenugreek gum, xanthan gum, seaweed gum, gellan gum, agar gum, cashew gum, carrageenan and curdlan. In embodiments, the polysaccharide gum matrix or scaffold is directionally manufactured so that the pores formed within the matrix or scaffold are directional. In embodiments, the directional matrix can be vertical, horizontal, radial, spherical, star-shaped, multi-directional or any other shape.

In embodiments of the present invention, these matrices or scaffolds provide a preferred cell culture environment. This cell culture environment may be appropriate for any type of cell in culture including primary cells, immortalized cells lines, groups of cells, tissues in culture, adherent cells, cells in suspension, cells growing in groups such as embryoid bodies, eukaryotic cells, prokaryotic cells, or any other cell type. In embodiments, this cell culture environment may be appropriate for adherent cells.

Some cell types have special requirements in culture. These cell culture preferences are exhibited by the cells as they take on different cell morphologies in culture, change their regenerative or reproductive characteristics, and change their metabolic and secretory characteristics. Embryonic stem cells, for example, require cell culture conditions which allow the cells to grow and propagate in an undifferentiated state until they are exposed to chemical and/or physical signals that allow them to differentiate into a desired cell type. Heart cells, for example, grown in an appropriate in vitro environment, will beat in unison with neighboring cells. For cells growing in culture to have characteristics in vitro that are relevant to their characteristics in vivo, cell culture conditions must be carefully controlled.

Hepatocytes, for example, have very specific cell culture requirements in order to maintain important in vivo characteristics in vitro. Hepatocytes are the primary functional cells of the liver and perform an array of metabolic, endocrine and secretory functions. Hepatocytes make up 60-80% of the cytoplasmic mass of the liver. They are exceptionally active in synthesis of proteins, cholesterol, bile salts and phospholipids for export, and are involved in protein storage and transformation of carbohydrates. In vivo, hepatocytes are responsible for detoxification, or modification and excretion of exogenous and endogenous substances from the body. Healthy hepatocytes in culture synthesize and secrete many proteins, including albumin and transferrin.

Primary and secondary cultures of hepatocytes have been used for pharmacology, toxicology and physiology studies, for studying the mechanisms of liver regeneration and differentiation, as well as for understanding factors which affect characteristics of hepatocytes in culture. Historically, primary hepatocytes have exhibited a limited replicating lifespan in culture. In addition, when stimulated to divide in culture they have generally lost differentiated functions such as the ability to synthesize and secrete albumin and transferrin. When cultured appropriately, cultured hepatocyte cells self-assemble into spheroidal structures that enhance liver-specific functions. When hepatocytes are not cultured appropriately, they form flat cells or cell clumps. The level of liver-specific activities, including albumin secretion and P450 activity, are lower with flat cell or cell clumps than those with spheroids.

When culturing cells of any cell type, a preferable cell culture environment promotes desirable cell characteristics in vitro. Such an environment that can be provided in a reproducible and inexpensive manner is desirable. In addition, cell culture vessels which incorporate these desirable environments are needed. And, methods of manufacturing and using cell culture vessels that incorporate desirable cell culture environments are needed.

In the following detailed description, for purposes of explanation and not limitation, exemplary embodiments disclosing specific details are set forth in order to provide a thorough understanding of embodiments of the present invention. However, it will be apparent to one having ordinary skill in the art that the present invention may be practiced in additional embodiments that depart from the specific details disclosed herein. In addition, detailed descriptions of well-known devices and methods may be omitted so as not to obscure the description of the present invention.

Embodiments of the present invention include matrices or scaffolds of material for cell culture. These matrices or scaffolds may be included in or introduced into cell culture vessels or containers. In an embodiment of the present invention, the matrix or scaffold is derived from at least one gum. While gums are discussed herein, it will be understood by those in the art that the term "gum" includes any composition containing plant gums or plant seed gums obtainable from natural plant gum sources, from recombinant sources, from synthetic sources, or from combinations of natural sources, recombinant sources and synthetic sources. Further, "gum" includes mixtures of various gums from different sources as well as gum compositions containing additional ingredients. Further, these gums can be modified by enzymatic or chemical manipulations to enhance desired chemical characteristics.

Naturally occurring gums are found in natural products. Examples of naturally occurring gums derived from plants include guar gum, locust bean gum (also known as carob bean gum, carob seed gum and carob gum), cassia gum, tragacanth gum, tara gum, karaya gum, gum acacia (also known as gum arabic), ghatti gum, cherry gum, cashew gum, apricot gum, tamarind gum, mesquite gum, larch gum, psyllium, fenugreek gum and tara gum. Galactomannan gums include locust bean gum (LBG), guar gum, cassia gum, tara gum, mesquite gum, and fenugreek gum. Gums that are derived from bacterial and algal sources include xanthan gum, seaweed gum, gellan gum, agar gum, carrageenan and curdlan. It will be understood by those of skill in the art that naturally occurring gums include mixtures of naturally occurring gums with various gums from different sources, and gums which have been collected from natural sources and then chemically purified, treated, modified, tuned and/or mixed with other ingredients to form suitable cell culture materials in embodiments of the present invention.

Naturally occurring gums can be produced as exudates of plants which may be produced by plants after a plant has been wounded. A wounded gum-producing plant produces an exudate in response to a wound (tears of gum).

These kinds of plant exudates may be harvested by wounding a plant or a plant seed and removing the exudates. These exudates can then be cleaned to remove dust, dirt and other impurities. The exudates may be dried, powdered and suspended in liquid. Further processing steps may include enzymatic treatment, filtration, centrifugation, hydrolysis and other chemical modifications.

Plant gums can also be derived from plant seeds. Seed-derived gums include guar (*Cyamopsis tetragonoloba*), locust bean or carob bean (*Ceratonia siliqua*), tara (*Caesalpinia spinosa*), fenugreek (*Trigonella foenum-graecom*), mesquite gum (*Prosopis* spp) and *Cassia* gum (*Cassia tora*). These are generally sub-tropical plants.

Gums are generally derived from the endosperm of the seeds. After removal of the shell and the germ of the seed, the endosperm is ground. The resulting powder (flour) can contain a high polysaccharide content which, upon mixing with water and/or other ingredients, can form a liquid gum substance. The suspension formed upon mixing the powdered gum with liquid can contain impurities such as cellulose, other plant matter, and various chemical impurities. The suspension can be treated to increase the purity of the gum suspension. For example, the liquid can be centrifuged, filtered, heated, or put through freeze-thaw cycles to remove plant debris and other impurities. An embodiment of the present invention includes a gum which has been purified by one of these steps, or by other means well known in the art. An embodiment of the present invention includes a gum which has been purified. Additional embodiments of the present invention include plant gums, naturally occurring gums and galactomannan gums which have been purified.

Powdered gum raw materials may also be purified or filtered according to particle size. For example sieves can be used to separate powdered gum material according to particle size. Particle sieve size openings of 250, 106, 53, 38 and 25 µm can be used to separate powdered gum material to create filtered particle size mixtures of between 106 and 250 µm, between 53 and 106 µm, between 38 and 53 µm, between 25 and 38 µm and <25 µm particles. These separated particle sizes, or mixtures of these particle sizes, can be used to produce embodiments of the three dimensional porous matrix of the present invention.

Plant gums have been used for centuries. Ancient Egyptians used locust bean gum to bind the wrapping of mummies. Plant gums are used in the cosmetic industry as thickeners, as hydrating agents, and as emulsification agents or foam stabilizers. Plant gums are used extensively commercially as food additives for their excellent properties including thickening, preventing the formation of ice crystals in frozen foods, retaining crispiness, retaining water, temperature tolerance and pH tolerance. Some gums, galactomannan gums for example, are non-ionic, and therefore are not affected by ionic strength or pH. Although they will degrade at pH and temperature extremes, in general, these conditions are not present in cell culture, and therefore do not pose a concern in cell culture applications.

Gum material can be purchased from chemical supply houses including Sigma-Aldrich, Fluka, TIC-Gums Inc. (Belcamp, Md.), Hercules (formally Aqualon Inc, Wilmington, Del.) and Gum Technology Corporation. Because these gums are used as food additives, and for industrial applications, these materials may be provided in less pure forms than might be necessary for laboratory uses. Therefore, additional purification steps and additional treatments may be necessary. Purification steps may include, for example, extraction in a solvent that is less polar than water, for example, ethanol. However, in the examples below, both purified and unpurified materials were utilized with favorable results. Locust bean gum is a galactomannan polysaccharide of the following formula:

FORMULA 1:

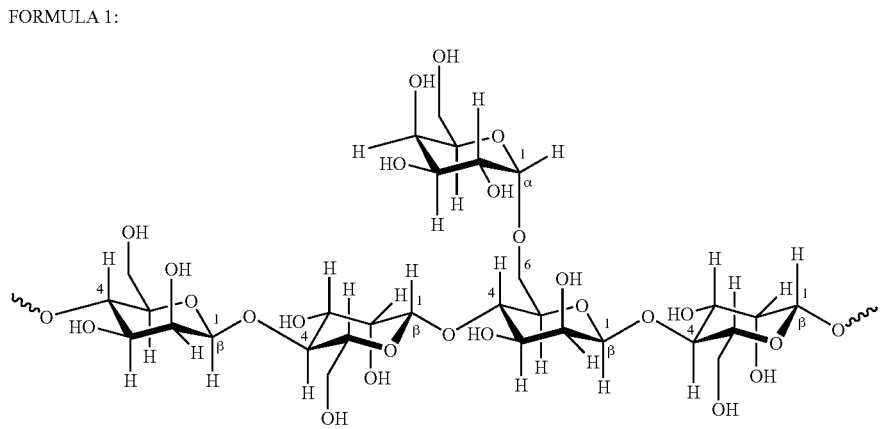

Locust bean gum (LBG) is a galactomannan polysaccharide consisting of mannopyranose backbone with branchpoints from their 6-positions linked to α-D-galactose residues. Locust bean gum has about 4 mannose residues for every galactose residue (a mannose/galactose ratio of about 4). Galactomannan gums include locust bean gum (LBG), guar gum, *cassia* gum, tara gum, mesquite gum, and fenugreek gum. Guar gum is a galactomannan polysaccharide consisting of a mannopyranose backbone. However, guar gum has more galactose branchpoints than locust bean gum. Guar gum has a mannose/galactose ratio of about 2. The mannose/galactose ratio is about 1:1 for mesquite gum and fenugreek gum, about 3:1 for tara gum and about 5:1 for Cassia gum. This difference in structure causes guar gum to be more soluble have a higher viscosity than locust bean gum. That is, locust bean gum is a galactomannan compound with lower galactose substitution and therefore it is "less stiff." Locust bean gum has more flexibility (lower modulus) than guar gum. Higher galactose substitution of these gums gives them improved solubility, dispersiveness and emulsification. Higher galactose substitution makes the galactomannan polysaccharides stiffer. Higher substitution lends the gum characteristics of higher viscosity and higher solubility.

Gums, including galactomannan gums may be derived from recombinant or synthetic sources. For example, galactomannose may be synthesized in vivo from GDP-mannose and UDP-galactose by the enzymes mannan synthase and galactosyltransferase. DNA coding for these proteins has been isolated and characterized, (US Publication 2004/0143871 incorporated herein by reference in its entirety) and recombinant plants transformed with these enzymes have been shown to express elevated levels of galactomannan. In addition, the degree of galactosylation of the mannopyranose backbone may be influenced by the presence (or absence) of alpha-galactosidase in vivo, (see Edwards et al. Plant Physiology (2004) 134: 1153-1162). Alpha-galactosidase removes galactose residues from the mannopyranose backbone. For example, seeds that naturally express galactomannans with a lower degree of galactosylation may express (or express more) alpha galactosidase, which removes galactose moieties from the mannopyranose backbone in those species of plant. The alpha-galactosidase enzyme may be used to reduce the presence of galactose on the mannopyranose backbone of naturally occurring galactomannose gums in a laboratory manipulation of the characteristics of the naturally occurring galactomannose gum. Embodiments of the present invention include gums, including naturally occurring gums and galactomannose gums, which have been treated with alpha-galactosidase to reduce the presence of galactose on the mannopyranose backbone. Embodiments of the present invention include gums which have been treated with alpha-galactosidase or other enzymes or chemical treatments, to "tune" the gums to provide the gum with desired characteristics as cell culture surfaces.

Without being held to any particular theory, galactomannan gums, with their mannose backbones and galactose sidechains, are thought to provide a surface for cell culture which presents galactose moieties to cells in culture. For some cell types, these galactose moieties may provide a surface or growth bed which encourages the growth of cells in culture. The inherent properties of the material, including low charge and hydrophilicity, make galactose based materials a suitable support for cells in culture.

Cultured hepatocytes may respond favorably to the presence of galactose in culture. The density and orientation of galactose moieties may regulate the attachment of cells such as hepatocytes to a cell culture substrate and improve the function of the cells in vitro. This may occur through the inhibition of integrin clustering and/or controlling cell-substrate and cell-cell interactions. The binding of multivalent galactose as a specific ligand to the asialoglycoprotein receptors (ASGPRs) on the surface of hepatocytes has been extensively studied and has been shown to improve hepatocyte adhesion while maintaining viability Although ASGPR does not physiologically function as an adhesion receptor, galactose-containing polymers have been used to induce the selective adhesion of primary hepatocytes to the substrate. The hepatocyte cell-cell interactions may result in promotion of the formation of spheroidal aggregates of hepatocytes in culture which in turn promotes the formation of bile canaliculi, gap junctions, tight junctions, and E-cadherins, resulting in enhanced hepatocyte function, and improved hepatocyte culture performance.

Embodiments of the gum matrices of the present invention also include gums which are purified or treated or modified by processes which may include enzymatic treatment, filtration, centrifugation, hydrolysis, freeze-thaw cycles, heating and chemical treatments or modifications, mixing gums with other gums, and mixtures of gums with other ingredients which optimize the cell culture characteristics of embodiments of the three dimensional matrices of the present invention.

Embodiments of the present invention include gum compounds which can be modified to optimize physical and chemical characteristics of cell culture matrices or scaffolds made from the gum compounds. Physical and chemical characteristics of the matrices or scaffolds of the present invention can be "tuned" by chemically modifying the gum material. "Tuned" or "tunable" used here means that gum material, obtained naturally or synthetically, can be modified, either physically or chemically to adjust the physical or chemical characteristics of the material to provide a cell culture substrate that promotes a desired cell culture environment for a particular cell type growing in a particular type of cell culture media, for a particular purpose. Physical characteristics of the material can be changed by changing the porosity of the matrix material, changing the three dimensional structure of the matrix, changing the modulus of the matrix, changing the charge density and distribution, surface energy, topology and porosity, or by changing other physical characteristics of the matrix. Chemical characteristics of the material can be changed by providing chemical crosslinkers in the material, adding or removing chemical groups from a particular matrix material, mixing different gum substances together, changing the type and density of receptor ligands present in the cell culture environment or by other chemical modifications. Chemical modifications can change the physical characteristics of embodiments of the present invention, and physical modifications can involve chemical modifications. Embodiments of the three dimensional porous cell culture matrix of the present invention can be tuned by, for example: changing the modulus of the naturally-occurring or synthetic material, changing the freeze-thaw conditions used to provide the matrix, changing the three-dimensional structure of the matrix, changing the porosity of the material, crosslinking the polysaccharide compounds, mixing multiple gum compounds together, adding additional compounds to the gum material in the matrix, changing the number or nature of the gum material by, for example, changing the number of mannose sidechains present on the galactose backbone of galactomannose gum material in the matrix, substituting sidechains, treating with enzymes to change the chemical nature of the material, or by any other method. Embodiments of the present invention include tuned or tunable cell culture matrices and scaffolds.

In embodiments of the present invention, the number and nature of galactose sidechains in a polysaccharide cell culture material may be changed. This modification affects the properties of galactose-presenting polysaccharide-based matrices. For example, in embodiments of the present invention, by adding and removing galactose polysaccharide sidechains from galactomannan polysaccharide gum cell culture matrices and scaffolds, and by changing the number of mannose groups per galactose, and by changing the nature of these sidechains, polysaccharide cell culture materials including galactomannan polysaccharide materials are tunable. In embodiments, the ratio of mannose:galactose may be from 1:1, 1:2, 1:3, 1:4, 1:5, 1:6, 1:7, 1:8, 1:9 or 1:10.

In another embodiment, the cell culture matrix has been treated to make a physically crosslinked system. A crosslinked gum is a physical gel which can be a gel or a hydrogel. The IUPAC Compendium of Chemical Terminology defines a gel as an elastic colloid or polymer network that is expanded throughout its whole volume by a fluid. The polymer network can be a network formed by covalent bonds or by physical aggregation with region of local order acting as network junctions. If the fluid is water it is a "hydrogel."

Treatments that provide crosslinking include exposure to particular temperature ranges, including heat, cold and freeze-thaw heat and cold cycles. Solutions of locust bean gum will gel under cryogenic treatment (freezing-thawing cycles). These freeze-thaw cycles create physical-gels or physically crosslinked networks. A solution of locust bean gum, if kept at room temperature will remain fluid. After prolonged storage (2-3 months) the solution will form a weak physical gel. Embodiments of the present invention include gum materials which have been treated or tuned to form a physical gel.

Embodiments of the present invention include cell culture matrices or scaffolds which are tuned to vary the modulus of the polymer, using cross-linking chemistry which may change the modulus of the cell culture material. Cross-linking methods include UV-induced cross-linking, and chemical cross-linking. Chemical agents such as borax (sodium borohydrate), gluteraldedye, epoxy derivatives, and other methods known in the art can be used. UV crosslinking methods also can be employed where a photoinitiator can be used in the gum or in the blend of gums to initiate gelling or cross-linking behavior. Embodiments of tuned gums of the present invention are gums which have been centrifuged, filtered, heated, frozen, freeze-thawed, chemically or enzymatically treated, exposed to light or otherwise altered, to improve the cell culture characteristics of a cell culture material made from the treated gum. Tuned gums of the present invention also include gums which are in gel or hydrogel form. Further, tuned gums of the present invention include galactomannan gums which have been centrifuged, filtered, heated, frozen, freeze-thawed, chemically or enzymatically treated, exposed to light or otherwise altered, and which are in gel or hydrogel form for use as a material for cell culture.

Embodiments of the present invention include mixtures of gums. Mixtures of gums can form cross-linked gel compositions. For example, charged polysaccharides such as xanthan gum or carrageenan or neutral polysaccharides with gelling behavior, such as agar or curdlan, can be mixed with galactomannan gums to form a blend that forms a gel at room temperature.

Embodiments of the present invention also include cell culture materials which have been tuned to change the charge characteristics of the material, which may be accomplished by changing the charge blending linear or branched charged polysaccharides in the material. Charged polysaccharides such as xanthan gum or carrageenan are mixed with a naturally occurring gum(s) to form a blend. Combinations of galactomannan gums with other gums such as carageenan and xanthan gums (charged polysaccharides) are capable of synergistic interactions. These gums in combination with locust bean gum form thermoreversible soft elastic gels without cryogenic (freeze-thaw) treatment. A greater proportion of guar gum (80:20) is required for optimal synergy for room temperature gellation compared to locust bean gum (50:50).

In another embodiment, a mixture (or blend) of at least two types of gum polysaccharides can be used on a surface of a substrate to form a cell-culture-friendly matrix. Providing a substrate with these gum polysaccharides materials individually or in a mixture of any combination of these polysaccharides can result in a matrix presenting varied amounts of galactose or other polysaccharide moieties. Mixtures or blends of at least two gums may include, for example, mixtures of two gums including: guar gum, locust bean gum (also known as carob bean gum, carob seed gum and carob gum), cassia gum, tragacanth gum, tara gum, karaya gum, gum acacia (also known as gum arabic), ghatti gum, cherry gum, apricot gum, tamarind gum, mesquite gum, larch gum, psyllium, cashew gum, fenugreek gum and tara gum. Gums that are derived from bacterial and algal sources include xanthan gum, seaweed gum, gellan gum, agar gum, carrageenan and curdlan.

In an alternative embodiment, the present invention provides a method to further tune the physical properties of a polysaccharide gum matrix. In one embodiment, conventional cross-linking methods are used to produce the polysaccharide matrix with varying modulus and surface energy (i.e., hydrophilicity). The cross-linking methods include physical, UV-induced cross-linking, and chemical cross-linking. In another embodiment, charged polysaccharides such as xanthan gum or carrageenan are mixed with a naturally occurring gum(s) to form a blend. The resultant blend is used to form a matrix having controlled charge density for cell culturing, including hepatocyte culturing. In another embodiment, linear neutral polysaccharides with gelling behavior, such as agar or curdlan, are mixed with the naturally occurring branched polysaccharide(s) to form a blend. The resultant blend is used to form a matrix having material properties such as modulus and stability for long term cell culturing. The three-dimensional matrix materials may be cross-linked with chemical treatment or with UV treatment. Chemical cross-linking may be accomplished by, for example, treating the gum material with gluteraldehyde. UV cross-linking may be accomplished by adding a photoinitiator to the composition, making the 3D scaffold, then exposing the 3D matrix to UV or fluorescent light to initiate the UV cross-linking reaction. In another embodiment, distinct methods are used to form a matrix having desired structural properties, such as topology and porosity. For example, directional solidification methods can be used to form 3-dimensional substrates. The three-dimensional matrices provide a scaffold for the cells. A three-dimensional matrix may provide a scaffold to guide the process of tissue formation, for example. Cells cultured on a three-dimensional matrix may grow in multiple layers to develop organotypic structures occurring in three dimensions such as ducts, plates, and spaces between plates that resemble sinusoidal areas, thereby forming, for example, new liver tissue. In again another embodiment, a combination of these methods can be used to fine-tune multiple material parameters.

In embodiments, three dimensional supports can be derived from natural branched polysaccharides using directional solidification or freezing or multi-directional freezing. The three dimensional nature of the matrix provides properties such as porosity, pore size and directionality of pores which allow cells to grow in more in vivo like environments. For example, directional pores may allow cells to grow in a porous scaffold, while allowing for the circulation of nutrients and gasses around the cells, through the porous structure. This circulation may allow for improved cell growth by allowing the cells improved access to nutrients and by allowing waste products and cellular byproducts to be washed away. Directional porous structure, or directional porosity includes porous structures that extend for example radially or longitudinally in a disc of porous material. Or, directional porous structure, or directional porosity may include porous structure that is a combination of radial and longitudinal structure, or directionally porous structure may include material that has multi-directional structure.

In embodiments, the scaffold or matrix of the present invention is a hydrogel that may float when placed in aqueous media in cell culture. In some embodiments, a floating scaffold may be preferred, to allow cells to fully integrate with the material, while enjoying access to media flowing around the cells from both the top and the bottom surfaces of a cell culture scaffold. In an additional embodiment, a device may be used to secure the matrix of the present invention to a cell culture surface. FIG. 1 illustrates an embodiment of a pinning device of the present invention. For example, a snap ring 10 may be used to secure the matrix to a substrate surface 20 in a cell culture well 30. The snap ring 10 may be made from Teflon® PTFE, or any other material or polymer that is non-reactive in an aqueous cell culture environment. The snap ring may be compressed or squeezed to fit inside the well. Once placed inside the well or cell culture container, pressure may be released from the snap ring, allowing it to fit snugly against the interior surface of the well. The snap ring may be the same height as the cell culture container or well. The snap ring may then be pushed down to pin or pinch the cell culture matrix to the bottom of the well. Solutions containing the cell cultures and other ingredients may then be added to the cell culture well. Any other device known in the art may be used to secure the matrix a cell culture surface including chemical adhesive, tacking devices applied from the cell culture surface of the matrix to the substrate surface, or projectiles or hooks molded into the substrate surface which extend into or through the matrix to affix it to the cell culture substrate. For example, small hooks or ridges formed during injection molding of the cell culture container may suffice to hold the matrix in place. Any of these devices, including a snap ring, or other devices suitable for pinning the three dimensional porous substrate to a cell culture container surface are embodiments of pinning devices of the present invention.

Figure 2A:
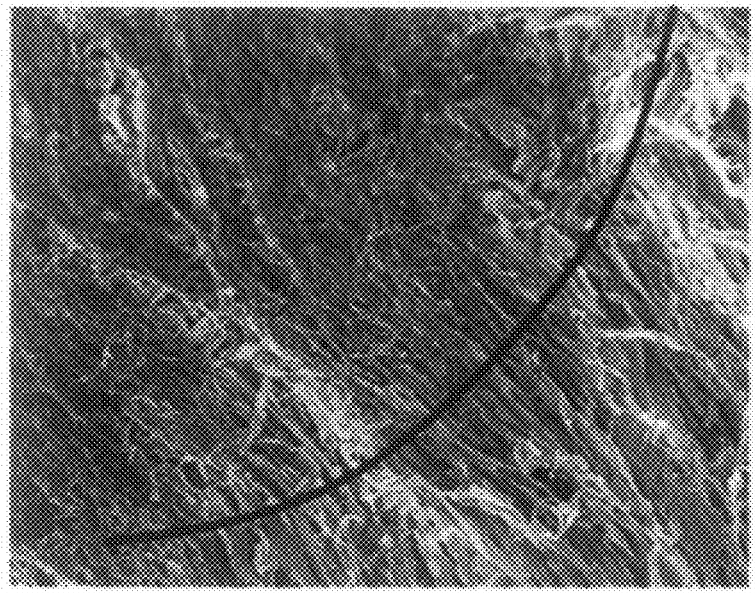
FIGS. 2A and 2B are photomicrographs of an embodiment of a matrix of the present invention, showing the porous nature of the matrix.
Figure 2B:
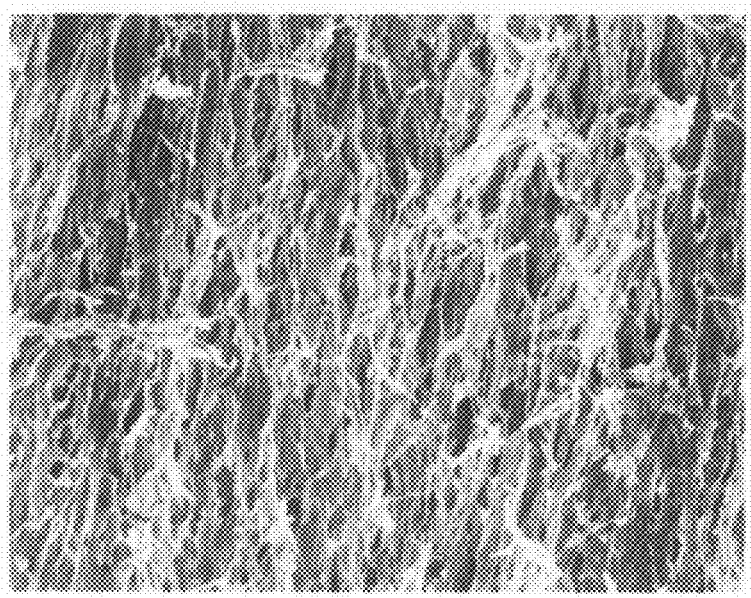

Directional solidification is a method for introducing directional structure into the cell culture matrices of the present invention. FIGS. 2A and 2B are SEM images of embodiments of the porous scaffold of the present invention in a dry state. FIG. 2A illustrates the top and side of a three dimensional porous scaffold or matrix. The line in FIG. 2A approximates the edge of the cylindrical sample. FIG. 2B illustrates a side of the three dimensional porous scaffold or matrix, and shows axially oriented porous structure in an embodiment of the directional three dimensional matrix of the present invention.

Directional solidification may be accomplished by applying cold to (or removing heat from) a matrix solution to allow the solution to freeze in a controlled manner. When a heat sink is applied from a direction, a freeze front is established. As the freeze front advances through the material, the solution of gum material freezes. Porous structures are formed in the gum material as it freezes. These porous structures are introduced into the material parallel to the direction of advancement of the freeze front (but perpendicular to the freeze front). The frozen material, which contains directional porous structures, may then be dried, and further treated.

Figure 3:
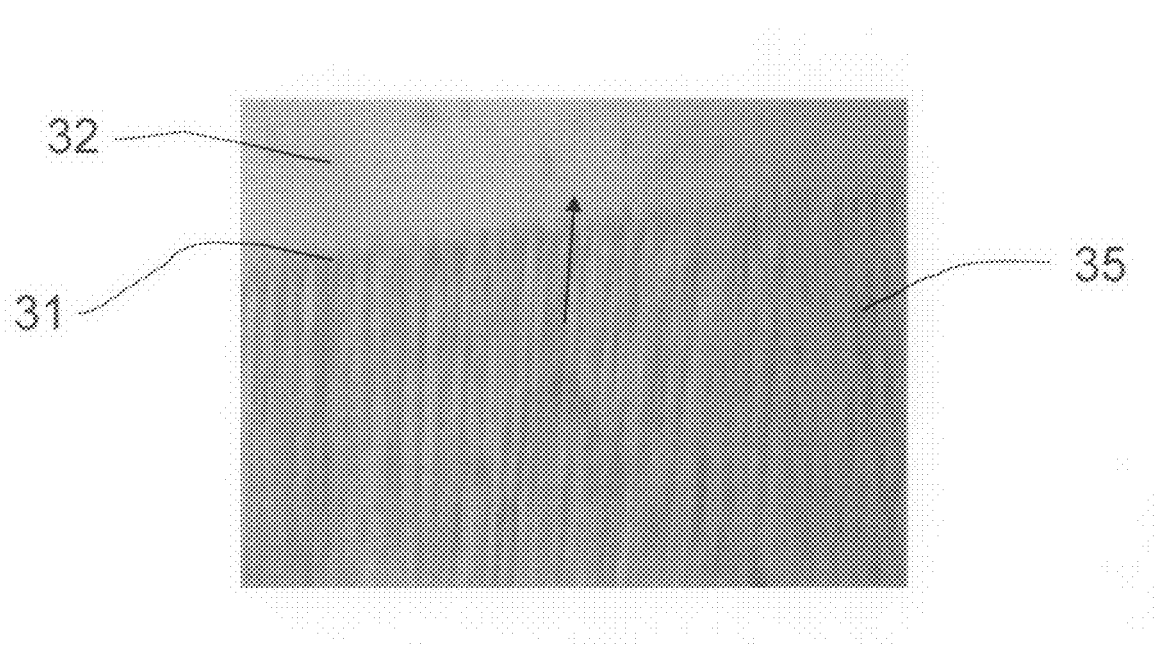
FIG. 3 is a photomicrograph showing the directional development of porous structure in an embodiment of a matrix of the present invention.

FIG. 3 is a photomicrograph showing the directional development of porous structure in an embodiment of a matrix of the present invention. As unfrozen material 32 freezes, a solid, porous matrix forms 35. Pores or columns are formed as the material freezes and the material changes from a liquid 32 to a solid phase 35. Pores are oriented parallel with the direction of the advancement of the freeze front 31, shown by the arrow in FIG. 3. By controlling the direction of the freeze front, using heat sinks to provide a temperature drop and a source of a freeze front and insulating material to define the boundaries of the freezing material, directionality of the pores and the porous structure of the scaffold or matrix can be controlled.

For example, by applying a conductive heat sink to the sides of a cylindrical container containing matrix solution, and by surrounding the top and bottom sides of the cylindrical container with non-conductive, insulative material, matrix solution inside a container may directionally freeze, following a freeze front that advances from the sides of the cylindrical container to the center of the cylindrical container. By freezing the material in this manner, radially oriented porous structure may be introduced into the three-dimensional material. By applying a heat sink to the bottom or underside of a cylindrical container which contains a matrix solution, and by insulating the sides and the top of the cylindrical container, a freeze front will advance through the matrix solution from the bottom to the top of the cylindrical container, introducing directional porous structure in the matrix in an axial direction away from the heat sink at the bottom of the cylindrical container. Using these methods, three-dimensional or porous structures may be formed which may encourage particular cells to grow or infiltrate the scaffolding and produce favorable cell culture conditions.

Figure 4:
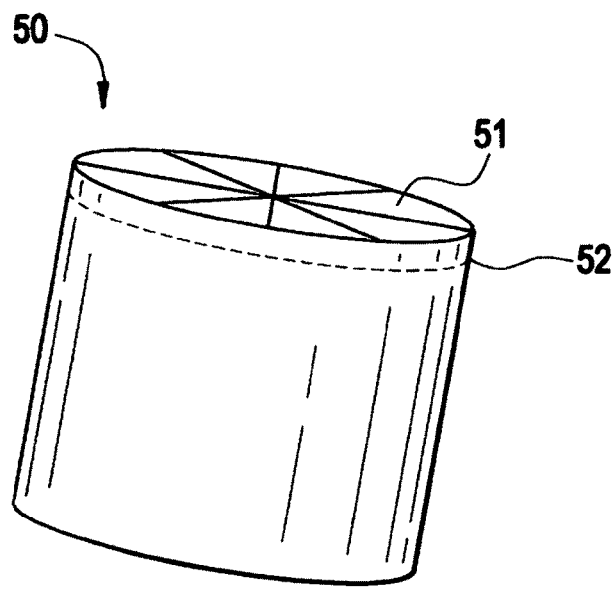
FIG. 4 is a perspective view of an embodiment of a matrix of the present invention where the directional porous structure is oriented radially.
Figure 5:
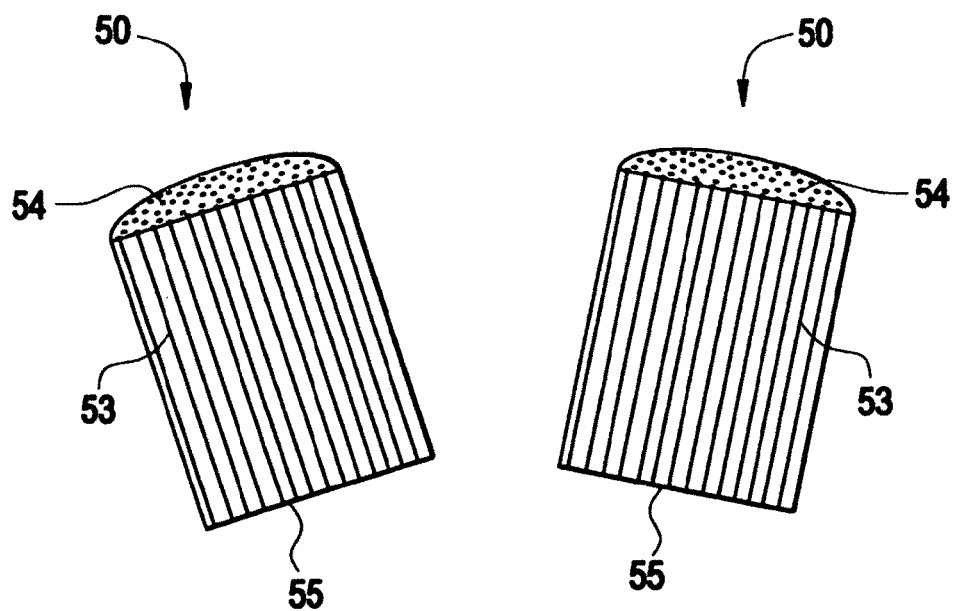
FIG. 5 is a cross-sectional view of an embodiment of a matrix of the present invention where the directional porous structure is oriented axially.

FIG. 4 is a perspective view of an embodiment of a matrix of the present invention. FIG. 4 shows the matrix 50, having radial pore structure 51 formed by radially freezing the material as described above. This material may be produced in a long cylinder to form a log of matrix material. A slice of this log 50 may be made, for example at line 52, to form a slice of directionally porous matrix material which can then be placed into a cell culture container or well. For example, in embodiments, a cell culture matrix may be a portion of matrix material cut from a larger manufactured portion of matrix material. The slice of directionally porous material may be held in the cell culture well by a pinning device such as a snap ring, or by any other pinning device. FIG. 5 is perspective view of an embodiment of a directional porous matrix material illustrating axially directed pore structure 53 oriented from a top end 54 to a bottom end 55 of the cell culture matrix.

Figure 6:
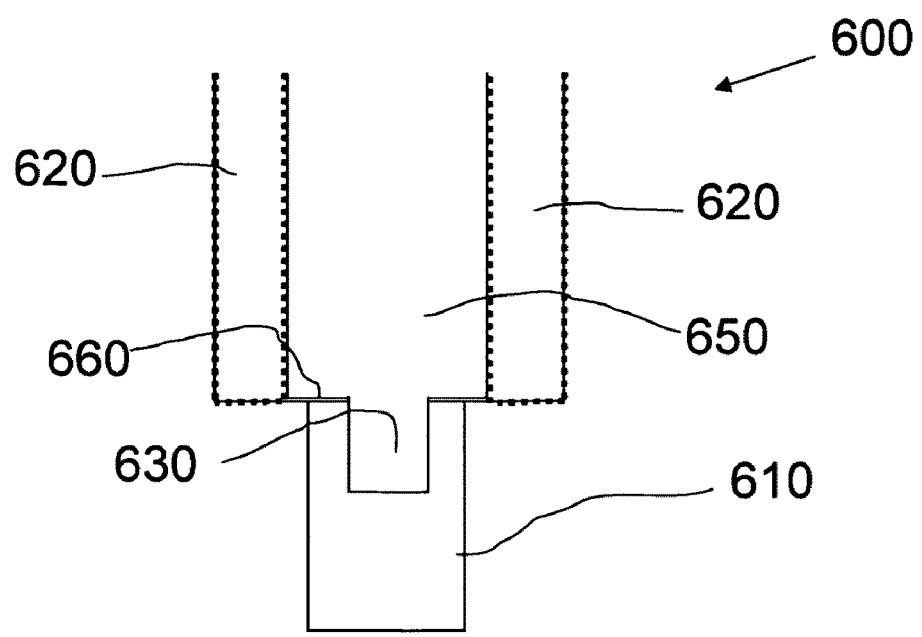
FIG. 6 is a cross-sectional view of a freeze capsule of the present invention.

Embodiments of the present invention include methods of making three dimensional porous substrates using directional freezing techniques. In embodiments, these directional freezing techniques may include introducing a liquid gum matrix mixture into a container, providing a heat sink to the container to reduce the temperature of the gum mixture and causing the gum mixture to freeze directionally. In embodiments, a freeze capsule may be used as an additional container to ensure that the direction of heat removal from the sample is predictable. FIG. 6 illustrates an embodiment of a freeze capsule 600. In embodiments, the freeze capsule 600 may be structured and arranged to contain a gum matrix solution container. The freeze capsule 600 may be constructed with a conductive heat sink 610 extending from the bottom of the freeze capsule. The heat sink may be a rod or a pin, as shown in FIG. 6, and may be made of conductive material such as copper, steel or aluminum. This heat sink 610 may be structured and arranged to extend into a cold environment, such as liquid nitrogen. The entire freeze capsule may be submerged into liquid nitrogen, or, in an alternative embodiment, just the heat sink 610, extending from the bottom of the freeze capsule 600, may be submerged in liquid nitrogen to create a cold surface 660 in the freeze capsule cavity 650. The freeze capsule 600 may also have non-conductive or insulated sides 620. The freeze capsule cavity 650 may be structured and arranged to hold a gum matrix container also referred to as a solution container. Importantly, the freeze capsule may be structured and arranged to form an intimate contact between the heat sink of the freeze capsule 610, and the heat sink of a gum matrix container. For example, the freeze capsule may have a recess 630 structured and arranged to receive a complimentary rod or pin extending from the bottom surface of the gum matrix container (see 201, FIG. 7A). Or, the heat sink of the freeze capsule may be a flat disc structured and arranged to engage with a solution container and the gum matrix container may have conductive material on the sides of the cylindrical gum matrix container, and have a bottom end made from insulative material, to allow the heat sink of the freeze capsule to be in intimate contact with the conductive sides of the cylindrical gum matrix container, to form radially oriented porous structures in the matrix material. As described herein, the freeze capsule and container are both cylindrical containers, but any shape of container may be used to form embodiments of the three dimensional matrices of the present invention. The insulated sides 620 may be made from insulation material such as polyurethane foam insulation. In addition, the insulated sidewalls 620 of the freeze container may be further contained in a housing (not shown) which may be structured and arranged to allow the freeze capsule to be introduced into and removed from an environment such as a liquid nitrogen bath. For example, the freeze capsule may be further contained within, for example, Teflon® PTFE tubing or other non-conductive material, and may be capped at one or both ends. The freeze capsule may also have an adaptor (not shown) to allow a chain or string to be attached to the freeze capsule so that the freeze capsule can be lowered into or lifted from a cold bath. When a solution container is introduced into this freeze capsule, and placed in intimate contact with the heat sink of the freeze capsule, directionality of the porous structure of the matrix can be controlled. The solution container can be structured and arranged to promote freeze directions in, for example, axial, radial or multiple directions.

Figure 7A:
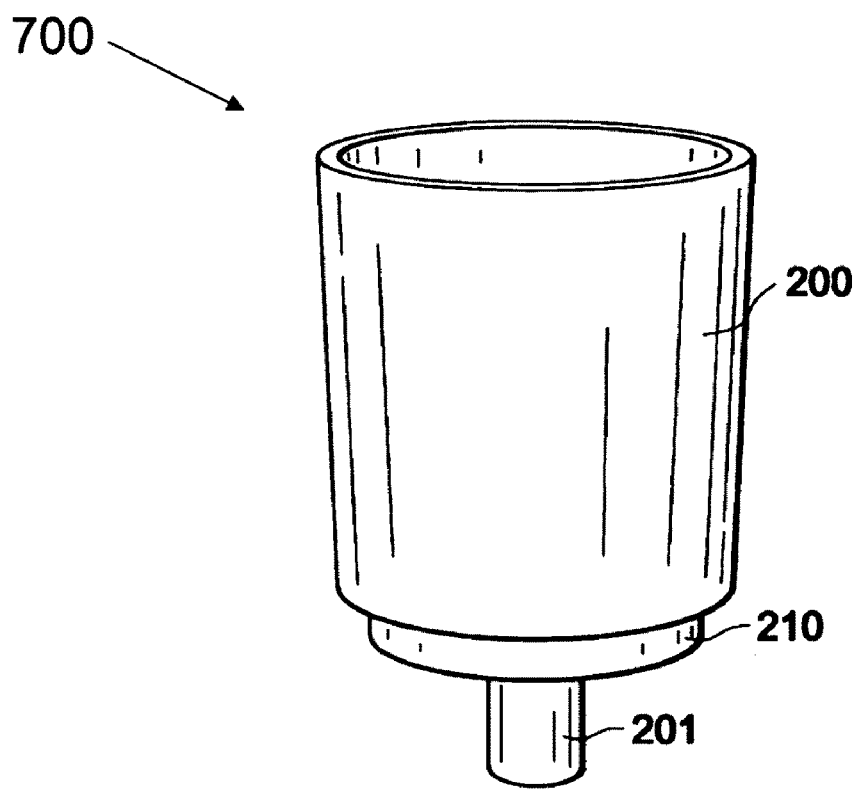
FIG. 7A is an illustration of an embodiment of the solution container and heat sink configuration of the present invention.
Figure 7B:
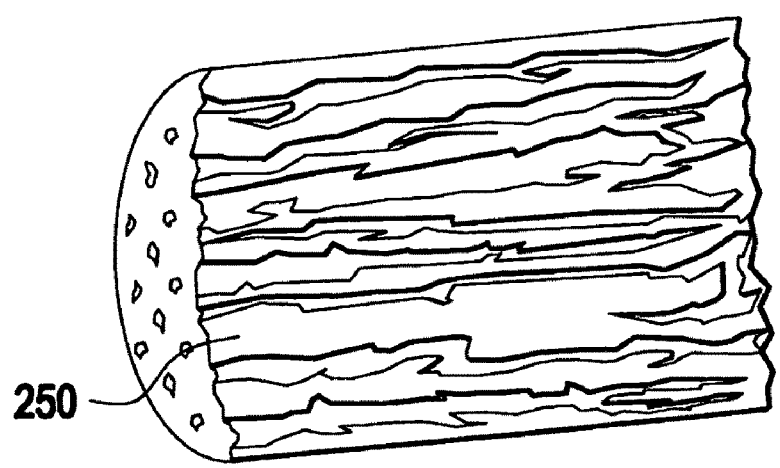
FIG. 7B illustrates an embodiment of a three-dimensional matrix that can be produced using an embodiment of the solution container and heat sink configuration of the present invention.

FIG. 7A illustrates an embodiment of the solution container 700 and heat sink configuration of the present invention. For example, as shown in the embodiment illustrated in FIG. 7A, the solution container 700 may have a heat sink 210 which is a disc or plate of conductive material such as copper, having a rod of conductive material 201 that extends down from the bottom of the container structured and arranged to fit snugly into the recess 630 (shown in FIG. 6) of the freeze capsule to form an intimate connection between the heat sink of the solution container and the heat sink of the freeze capsule. As the heat sink of the freeze capsule (610, shown in FIG. 6) is submerged into a cold bath, the conductive heat sink of the freeze capsule bottom removes heat from the bottom of the freeze capsule, and from the bottom of the solution container. The solution container may be cylindrical, and the length or wall of the cylinder 200 may be made from an insulated, non-conductive material such as polyvinyl chloride pipe. When the solution container shown in FIG. 7 is inserted into the freeze capsule illustrated in FIG. 6, and the freeze capsule is lowered into a cold bath, a directionally porous matrix material may be formed in the solution container. Because the freeze front of the freezing material will be advancing from the bottom surface of the cylindrical solution container, axially oriented porous matrix material 250 will be formed, as shown in FIG. 7B.

While FIG. 7 illustrates a disc-shaped heat sink at the bottom of a cylindrical solution container, embodiments of the heat sink and solution container of the present invention may be of any shape or configuration. For example, the heat sink may project into the solution container or the heat sink may surround the solution container. The heat sink may extend from the solution container to allow one end of the solution container to be immersed directly into, for example, ice or dry ice or liquid nitrogen, to provide a heat sink. As the heat sink cools, gum material may cool, and may freeze in a front extending from the cooling surface of the heat sink, to create a directional three dimensional matrix in the gum mixture as it freezes. The directional three dimensional matrix has pores or structures that extend in a direction perpendicular to the freeze front. The term "pores," for the purposes of this disclosure, are not clearly defined cylindrical structures, but are irregular structures that may create a tortuous path through the material. For example, a three dimensional cell culture matrix may have a longitudinal orientation or an axial orientation.

Figure 8A:
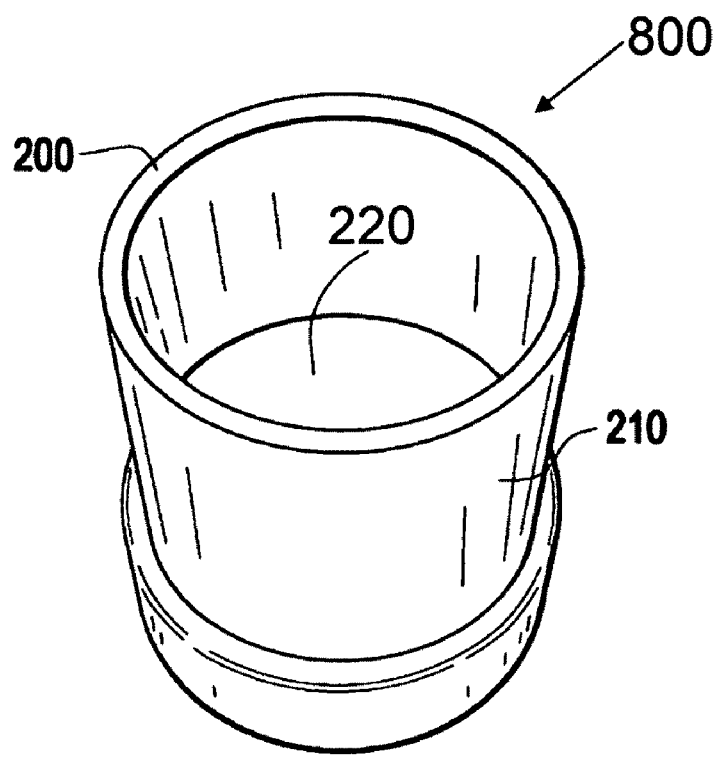
FIG. 8A is an illustration of an embodiment of another solution container and heat sink configuration of the present invention.
Figure 8B:
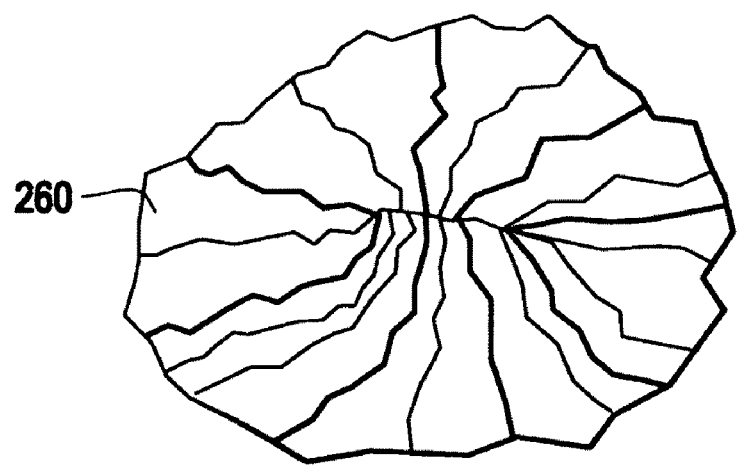
FIG. 8B illustrates an embodiment of a three-dimensional matrix that can be produced using an embodiment of the container and heat sink configuration of the present invention.

FIG. 8A illustrates another embodiment of the solution container 800 of the present invention. In this embodiment, the length or wall 200 of the cylindrical solution container is the heat sink 210. In this embodiment, the cylindrical wall 200 of the solution container may be made from conductive material such as copper. The bottom surface 220 of the solution container may be made from non-conductive material. The copper cylindrical solution container, when in contact with a bottom surface (not shown) of a freeze capsule 600 (shown in FIG. 6) may provide a solution container having a heat sink as a wall 200, allowing for gum material contained within the solution container to freeze in a radial orientation, 260, as illustrated in FIG. 8B.

Figure 9A:
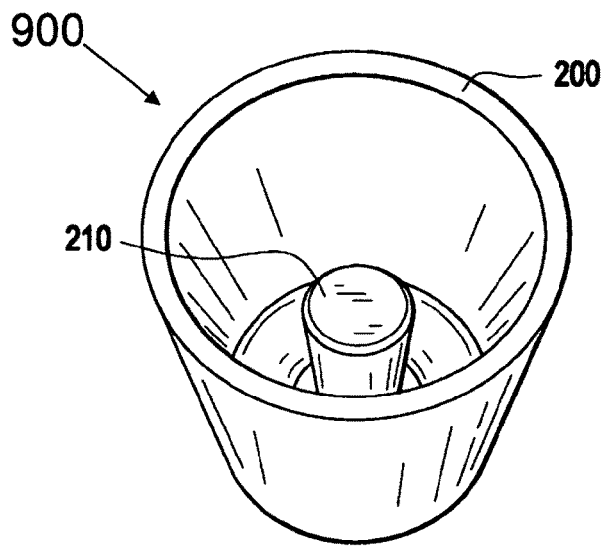
FIG. 9A is an illustration of another embodiment of a solution container and heat sink configuration of the present invention.
Figure 9B:
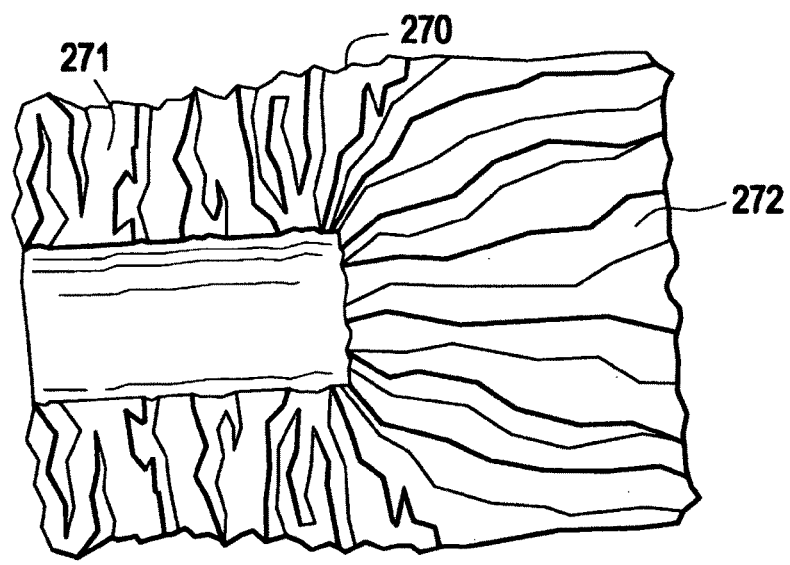
FIG. 9B illustrates an embodiment of a three-dimensional matrix that can be produced using an embodiment of the freeze capsule and heat sink configuration of the present invention.

FIG. 9A illustrates another embodiment of the solution container 900 and heat sink of the present invention. In this embodiment, the heat sink 210 may be a copper cylinder or rod that extends into the solution container 900. In this embodiment, the wall 200 of the cylindrical solution container may be made from a non-conductive material. FIG. 9B illustrates a directional three dimensional matrix that may be formed using the heat sink 210 and solution container configuration 900 illustrated in FIG. 9A. In the directional three dimensional matrix illustrated in FIG. 9B, the three dimensional structure of the matrix may have a radial orientation 271 which changes to an axial or longitudinal orientation 272. This is an example of multi-directional porous structure. In additional embodiments, more than one heat sink may be extend into the solution container 900. By incorporating multiple heat sinks, in different orientations and geometries, complex three dimensional directional matrices may be produced. For example, the three dimensional matrix may be oriented axially, radially, or have a combination of orientations. Or, in additional embodiments, a solution container may be made entirely from conductive material, or entirely from non-conductive material. When this solution container is submerged in a cold bath, a multi-directional porous structure is formed. Or, the sides and bottom surfaces of the solution container may be made from conductive material, or any material, forming heat sink structures. When this solution container is lowered into a cold bath, multi-directional three dimensional porous matrix structure is formed.

Embodiments of the present invention include substrates which provide support for a galactose polysaccharide matrix. These substrates may be plastic or polymeric. The substrates may be surfaces or vessels or containers and include those composed of polyester, polystyrene, polypropylene, polymethyl methacrylate, polyvinyl chloride, polymethyl pentene, polyethylene, polycarbonate, polyolefin, polyolefin copolymers, polysulfone, polystyrene copolymers (e.g., SAN and ABS), polypropylene copolymers, ethylene/vinyl acetate copolymer, polyamides, fluoropolymers, polyvinylidene fluoride, polytetrafluoroethylene, silicones, and elastomers, including silicone, hydrocarbon, and fluorocarbon elastomers. Those of skill in the art will recognize that many materials may be used as substrates or supports for the matrices or scaffolds of the present invention.

Embodiments of the present invention include inorganic substrates which form cell culture surfaces or vessels or containers and include those comprising or composed of inorganic materials such as metals, semiconductor materials, glass and ceramic materials. Examples of metals that can be used as surface or substrate materials include oxides of gold, platinum, nickel, palladium, aluminum, chromium, steel, and gallium arsenide. Semiconductor materials used for substrate or surface material can include silicon and germanium. Glass and ceramic materials that can be used for surface or substrate material can include quartz, glass, porcelain, alkaline earth aluminoborosilicate glass and other mixed oxides. Further examples of inorganic substrate materials include graphite, zinc selenide, mica, silica, lithium niobate, and inorganic single crystal materials.

Embodiments of the present invention include labware or cell culture vessels made from a substrate or combination of substrates, where the labware or cell culture vessel has been provided with a cell culture matrix or scaffold of the present invention. Labware includes slides, cell culture plates, multiwell plates, 6-well plates, 12-well plates, 24-well plates, 48-well plates, 96-well plates, 384-well plates, 136 well plates, flasks, multi-layer flasks, bioreactors, and other surfaces or containers or vessels used for cell culture. In addition, embodiments of the present invention may include inserts that are placed into cell culture containers or wells which allow for directional cell culture. For example, embodiments of three dimensional matrices of the present invention may be applied to Transwell® products sold by Corning Incorporated, which can then be introduced into cell culture dishes or wells. These cell culture vessels may provide solution containers.

Alternate embodiments of the present invention include gum or naturally occurring gum or galactomannan gum cell culture matrices or scaffolds for use in culturing cells including, but not limited to, stem cells, committed stem cells, differentiated cells, and tumor cells. Examples of stem cells include, but are not limited to, embryonic stem cells, bone marrow stem cells and umbilical cord stem cells. Other examples of cells used in various embodiments include, but are not limited to, myoblasts, neuroblasts, fibroblasts, glioblasts, germ cells, hepatocytes, chondrocytes, keratinocytes, smooth muscle cells, cardiac muscle cells, connective tissue cells, glial cells, epithelial cells, endothelial cells, hormone-secreting cells, cells of the immune system, and neurons. In one aspect, bone cells such as osteoclasts, osteocytes, and osteoblasts can be cultured with the coated substrates produced herein.

Cells useful herein can be cultured in vitro, derived from a natural source, genetically engineered, or produced by any other means. Any source of cells can be used. Atypical or abnormal cells such as tumor cells can also be used herein. Tumor cells cultured on coated substrates described herein may provide more accurate representations of the native tumor environment in the body for the assessment of drug treatments. Growth of tumor cells on the substrates described herein may facilitate characterization of biochemical pathways and activities of the tumor, including gene expression, receptor expression, and polypeptide production, in an in vivo-like environment allowing for the development of drugs that specifically target the tumor.

Cells that have been genetically engineered can also be used. Engineering involves programming the cell to express one or more genes, repressing the expression of one or more genes, or both. Genetic engineering can involve, for example, adding or removing genetic material to or from a cell, altering existing genetic material, or both. Embodiments in which cells are transfected or otherwise engineered to express a gene can use transiently or permanently transfected genes, or both. Gene sequences may be full or partial length, cloned or naturally occurring.

Hepatocytes have been shown here as an exemplary cell type. Although hepatocytes are shown, any other cell or cell type may be grown in culture using embodiments of the present invention. Hepatocytes represent significant cell culture challenges because long term cell culture of primary and secondary hepatocytes generally results in cells which lose their physiological characteristics over time. Primary hepatocytes are anchorage dependent cells, or adherent cells, and are very difficult to maintain in vitro, losing their adult liver morphology and differentiated functions when cultured in monolayers or suspension. Several cell culture models are being investigated based on complex hepatocyte microenvironment. These include studying various components in extracellular matrix, modifying cell culture media with addition of low concentrations of hormones, corticosteroids, cytokines, vitamins, or amino acids, and understanding cell-cell interactions, both homotypic (hepatocyte-hepatocyte) and heterotypic (hepatocyte-nonparenchymal cell). All these have shown that hepatocyte function and proliferation in vitro are modulated by cell attachment, cell shape and cell spreading through cell-cell and cell-matrix interactions and that the hepatocyte behavior in vitro can be modified by the culture medium and the cell culture substrate. It is desirable to develop cell culture conditions that provide difficult to culture cells like hepatocytes with an environment that allows the cells to maintain in vivo-specific functions (in the case of hepatocytes, liver-specific functions) in primary and secondary culture achieved by using non-animal derived materials and suitable culture media. For example, on untreated normal polystyrene 2D surface such as tissue culture treated (TCT) polystyrene, hepatocyte cells show flat morphology, great growth rate and low hepatocyte-specific function. By comparison, on Matrigel™ (Becton Dickonson Biosciences), cultured hepatocyte cells show spheroid structure, moderate/low growth rate and high hepatocyte-specific function (data not shown).

For example, an embodiment of the cell culture surface matrix or scaffold of the present invention can be tuned to create conditions that encourage the formation of spheroidal morphology or colony cell culture with hepatocytes and induce the culture of more functionally in-vivo-like cells. These tuned cell culture matrices may promote maintenance of cell-cell interactions (e.g. formation of bile canaliculi, cytoskeletal arrangements) and liver specific cell function (e.g. albumin production) in hepatocytes. For example, by using varied galactose substitutions, the stiffness and solubility of the resultant matrix can be controlled. The higher the substitution, the higher the stiffness, and the better the solubility, dispersiveness and emulsification (i.e., decreased flexibility). Embodiments of the present invention provide a polysaccharide matrix for more in vivo-like hepatocyte cultures with extended viability (in the differentiated state).

Embodiments of the present invention include cell culture matrices which include at least one biologically active molecule. Inclusion of a biologically active molecule may promote cell adhesion, proliferation or survival. Or, the inclusion of a biologically active molecule might improve function of cells in culture. Bioactive molecules include human or veterinary therapeutics, nutraceuticals, vitamins, salts, electrolytes, amino acids, peptides, polypeptides, proteins, carbohydrates, lipids, polysaccharides, nucleic acids, nucleotides, polynucleotides, glycoproteins, lipoproteins, glycolipids, glycosaminoglycans, proteoglycans, growth factors, differentiation factors, hormones, neurotransmitters, pheromones, chalcones, prostaglandins, immunoglobulins, monokines and other cytokines, humectants, minerals, electrically and magnetically reactive materials, light sensitive materials, antioxidants, molecules that may be metabolized as a source of cellular energy, antigens, and any molecules that can cause a cellular or physiological response. Any combination of molecules can be used, as well as agonists or antagonists of these molecules. Glycoaminoglycans include glycoproteins, proteoglycans, and hyaluronan. Polysaccharides include cellulose, starch, alginic acid, chytosan, or hyaluronan. Cytokines include, but are not limited to, cardiotrophin, stromal cell derived factor, macrophage derived chemokine (MDC), melanoma growth stimulatory activity (MGSA), macrophage inflammatory proteins 1 alpha (MIP-1 alpha), 2, 3 alpha, 3 beta, 4 and 5, interleukin (IL) 1, IL-2, IL-3, IL-4, IL-5, IL-6, IL-7, IL-8, IL-9, IL-10, IL-11, IL-12, IL-13, TNF-alpha, and TNF-beta. Immunoglobulins useful herein include, but are not limited to, IgG, IgA, IgM, IgD, IgE, and mixtures thereof. Amino acids, peptides, polypeptides, and proteins can include any type of such molecules of any size and complexity as well as combinations of such molecules. Examples include, but are not limited to, structural proteins, enzymes, and peptide hormones. These compounds can be mixed with the gum compounds as they are being prepared, or can be added to the surface of the cell culture matrix after it has been applied to a cell culture surface.

The term bioactive molecule also includes fibrous proteins, adhesion proteins, adhesive compounds, deadhesive compounds, and targeting compounds. Fibrous proteins include collagen and elastin. Adhesion/deadhesion compounds include fibronectin, laminin, thrombospondin and tenascin C. Adhesive proteins include actin, fibrin, fibrinogen, fibronectin, vitronectin, laminin, cadherins, selectins, intracellular adhesion molecules 1, 2, and 3, and cell-matrix adhesion receptors including but not limited to integrins such as $\alpha_5\beta_1$, $\alpha_6\beta_1$, $\alpha_7\beta_1$, $\alpha_4\beta_2$, $\alpha_2\beta_3$, and $\alpha_6\beta_4$.

The term bioactive molecule also includes leptin, leukemia inhibitory factor (LIF), RGD peptide, tumor necrosis factor alpha and beta, endostatin, angiostatin, thrombospondin, osteogenic protein-1, bone morphogenic proteins 2 and 7, osteonectin, somatomedin-like peptide, osteocalcin, interferon alpha, interferon alpha A, interferon beta, interferon gamma, interferon 1 alpha, and interleukins 2, 3, 4, 5 6, 7, 8, 9, 10, 11, 12, 13, 15, 16, 17 and 18.

The term "growth factor" as used herein means a bioactive molecule that promotes the proliferation of a cell or tissue. Growth factors useful herein include, but are not limited to, transforming growth factor-alpha. (TGF-alpha), transforming growth factor-beta. (TGF-beta), platelet-derived growth factors including the AA, AB and BB isoforms (PDGF), fibroblast growth factors (FGF), including FGF acidic isoforms 1 and 2, FGF basic form 2, and FGF 4, 8, 9 and 10, nerve growth factors (NGF) including NGF 2.5 s, NGF 7.0 s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8, VEGF-E, granulocyte colony stimulating factor (G-CSF), insulin like growth factor (IGF) I and II, hepatocyte growth factor (HGF), glial neurotrophic growth factor (GDNF), stem cell factor (SCF), keratinocyte growth factor (KGF), transforming growth factors (TGF), including TGFs alpha, beta, beta1, beta2, and beta3, skeletal growth factor, bone matrix derived growth factors, and bone derived growth factors and mixtures thereof. Some growth factors can also promote differentiation of a cell or tissue. TGF, for example, can promote growth and/or differentiation of a cell or tissue. Some preferred growth factors include VEGF, NGFs, PDGF-AA, PDGF-BB, PDGF-AB, FGFb, FGFa, HGF, and BGF.

The term "differentiation factor" as used herein means a bioactive molecule that promotes the differentiation of cells or tissues. The term includes, but is not limited to, neurotrophin, colony stimulating factor (CSF), or transforming growth factor. CSF includes granulocyte-CSF, macrophage-CSF, granulocyte-macrophage-CSF, erythropoietin, and IL-3. Some differentiation factors may also promote the growth of a cell or tissue. TGF and IL-3, for example, can promote differentiation and/or growth of cells.

The term "adhesive compound" as used herein means a bioactive molecule that promotes attachment of a cell or tissue to a fiber surface comprising the adhesive compound. Examples of adhesive compounds include, but are not limited to, fibronectin, vitronectin, and laminin.

The term "deadhesive compound" as used herein means a bioactive molecule that promotes the detachment of a cell or tissue from a fiber comprising the deadhesive compound. Examples of deadhesive compounds include, but are not limited to, thrombospondin and tenascin C.

The term "targeting compound" as used herein means a bioactive molecule that functions as a signaling molecule inducing recruitment and/or attachment of cells or tissues to a fiber comprising the targeting compound. Examples of targeting compounds and their cognate receptors include attachment peptides including RGD peptide derived from fibronectin and integrins, growth factors including EGF and EGF receptor, and hormones including insulin and insulin receptor.

In another aspect, the invention provides methods for determining an interaction between a cell line and a drug. Methods steps may include (a) depositing cells on an embodiment of the matrix of the present invention; (b) contacting the deposited cells with a drug; and (c) identifying a response produced by the deposited cells upon contact with the drug.

With a known cell line immobilized on or in embodiments of the three-dimensional porous cell culture system of the present invention, it is possible to screen the activity of several drugs when the drug interacts with the immobilized cells. Depending upon the cells and drugs to be tested, the cell-drug interaction can be detected and measured using a variety of techniques. For example, a drug can be added to the cell culture media bathing cells in culture, the cell can metabolize the drug to produce metabolites that can be readily detected by examining media extracted from the cell culture, after a period of time. Alternatively, the drug can induce the cells to produce proteins or other biomolecules. The produced proteins or biomolecules can then be detected in the media removed from the cell culture. In addition, the cells can be extracted from the culture system, and analyzed for gene expression or other biomarkers, related to exposure to drugs or compounds.

The substrates can be used in high throughput applications for analyzing drug/cell interactions. Cells can be grown in the scaffolds and matrices of the present invention within multi-well plates used in high throughput applications. Cells can then be exposed to a drug, media can be removed from these high-throughput cultures, and the removed media can be analyzed for the presence of metabolites, proteins or other biomolecules. Increasing the population of cells per well, or increasing in vivo-like nature of cells in culture, would serve to increase the value of signals measured by these techniques.

Embodiments of the present invention also include hepatocyte cell cultures which can be used as bio-artificial livers for use in compound toxicity evaluation, compound metabolisms, and protein synthesis. Hepatocytes have the ability to metabolize, detoxify, and inactivate exogenous compounds such as drugs and insecticides, and endogenous compounds such as steroids. The drainage of the intestinal venous blood into the liver requires efficient detoxification of miscellaneous absorbed substances to maintain homeostasis and protect the body against ingested toxins. One of the detoxifying functions of hepatocytes is to modify ammonia into urea for excretion.

In another aspect, a method for growing cells or tissue is described, comprising: (a) depositing cells on an embodiment of the matrix described herein; (b) adding cell culture media; and (c) incubating the cells. It is also contemplated that viable cells can be deposited on the matrix substrates produced herein and cultured under conditions that promote tissue growth. Tissue grown (i.e., tissue engineering) from any of the cells described above is contemplated with embodiments of matrix substrates of the present invention. The matrix substrates can support many different kinds of precursor cells, and the substrates can guide the development of new tissue. The production of tissues has numerous applications in wound healing. It is contemplated that tissue growth can be performed in vivo or ex vivo.

Like hepatocytes, other cell types in culture take on spheroidal cell morphology as a preferred and more in-vivo-like cell culture state. Therefore embodiments of the cell culture matrices of the present invention may be used for multiple cell types. The invention can also be used for cell types that prefer the "spheroidal" morphology shown by hepatocytes as a mode of their own function.

WORKING EXAMPLES

The following examples are included to demonstrate embodiments of the invention and are not intended to limit the scope of the invention in any way. It should be appreciated by those of skill in the art that the techniques disclosed in the examples which follow represent techniques discovered by the inventors to function well in the practice the invention. However, those of skill in the art should, in light of the present disclosure, appreciate that many changes can be made in the specific embodiments which are disclosed and still obtain a like or similar result without departing from the spirit and scope of the invention.

Example 1

Locust Bean Gum Three Dimensional Matrix Preparation

Example 1a

Preparation of Material

A weighed amount of locust bean gum powder (white-beige) LBG (Sigma-Aldrich, Catalog #G0753, Lot#125K0091 or Catalog #62631 Fluka Chemicals, Lot #1301452, also available from Hercules Incorporated, Aqualon Division (Wilmington, Del.)) was dispersed in DI water to form 1-5 wt % solutions (with and without pH adjustment to 7). The suspensions were degassed by sonication for about 5 minutes. The vessel was sealed and the inhomogeneous solution was stirred at RT first (2-3 h) and then the temperature was increased to 100-120° C. with continuous stirring at that temperature for 15 min.

Sodium benzoate was added to the solution to prevent bacterial degradation. The locust bean gum weighed powder was additionally processed by centrifugation. Chemical purification and/or filtration can also be used as in, for example, steps disclosed in Pai, et al, *Carbohydrate Polymers* 49 (2002) 207-216. Centrifugation was accomplished by centrifuging the locust bean gum solution at 4000 rpm for 20 minutes to separate out impurities. The supernatant containing the locust bean gum polymer was then separated from the pellet, which mainly contained impurities.

The locust bean gum can also be purified chemically by ethanol extraction, with or without a centrifugation step. The locust bean gum solution can be poured into an excess of ethanol, causing the locust bean gum to precipitate. The precipitate can then be lyophilized (at RT for 24 hours). The resulting powder can be further processed by mechanical means such as pulverizing the precipitate to form a fine powder.

Example 1b

Cross-Linking

Locust bean gum, prepared according to Example 1a, were exposed to a chemical cross-linking step using a gluteraldehyde (acid) 5-0.1% in ethanol. The treatment time varied from 5-30 min. The gluteraldehyde solution was removed. Wash steps were performed in 100% ethanol, then 70% ethanol and finally water. The Locust Bean Gum was then dried by lyophilization.

Example 2

Preparation of Matrices

Example 2a

Multi-Directional Freezing

Suspensions of locust bean gum were added into individual wells of 96 well plates, varying the amount of material. The wells were loosely wrapped with aluminum foil to hold the matrix disc in place after drying. Aluminum-wrapped wells were inserted into a freeze capsule. The top of the wells were open but in line of sight of the top of the freezing capsule. The freeze capsule was lowered into a small dewar containing liquid nitrogen. The capsule was positioned initially in contact with the surface or below the surface of the liquid nitrogen. At this point the cell culture wells experience rapid multi-directional freezing at temperatures from 0° C. to −100° C. during the period of immersion of 15 minutes. At the completion of the freezing cycle of 15 minutes the wells were removed from the capsule and immediately transferred to the freeze dry process.

The freeze dry process was conducted by placing the wells into a lyophilization holding or process tube which was maintained at a temperature of −3° C. to prevent samples from melting during lyophilization. Samples were held at this temperature and under vacuum for approximately 24 hours until the process vacuum reached a level of <5 milliTorr. This level of vacuum indicated that the water contained in the sample has sublimed and that the samples were dry. Samples were then removed from the freeze dry process, the aluminum foil removed. A snap ring, as shown in FIG. 1, was inserted into the wells to hold the matrices in place.

Example 2b

Uni-Directional Freezing (Axial)

Suspensions were added into individual wells varying the amount of material. One well was inserted into a freeze capsule with the bottom of the well in intimate contact with a heat sink. The top and sides of the well were exposed to non-conductive or insulated surfaces. The capsule was then lowered into a small dewar containing liquid nitrogen. The capsule was positioned just above the level of liquid nitrogen with a metallic heat sink initially in contact with the surface or below the surface of the liquid nitrogen. At this point the cell culture wells experienced rapid uni-directional (axial: from bottom to top), as shown in FIG. 7B freezing at temperatures from 0° C. to −100° C. during the period of immersion of 15 minutes. At the completion of the freezing cycle of 15 minutes the wells were removed from the capsule, loosely but quickly wrapped with aluminum foil to hold the disc in place in the well during drying, and then immediately transferred to the freeze dry process. Lyophilization was then completed as described in the previous process description. The resulting cell culture porous scaffold was ~1-10 mm thick and opaque when dry and greater than 2-10 mm, thick and opaque when wet.

Example 2c

Uni-Directional Freezing (Radial)

Suspensions, prepared as above, were added onto individual wells varying the amount of material added into different wells. One well was inserted into a freeze capsule with only the sides of the well in intimate contact with a conductive outer well layer which was itself in intimate contact with the capsule and a heat sink, as shown in FIG. 8A. The bottom of the well was a non-conductive or insulated surfaces. The capsule was then lowered into a small dewar containing liquid nitrogen. The metallic heat sink was initially in contact with the surface or below the surface of the liquid nitrogen. At this point the cell culture wells experienced rapid uni-directional (radial: from the sides to the center) freezing at temperatures from 0° C. to −100° C. during the period of immersion of 15 minutes, as shown in FIG. 8B. At the completion of the freezing cycle of 15 minutes the wells were removed from the capsule, loosely but quickly wrapped with aluminum foil to hold the disc in place in the well during drying, and then immediately transferred to the freeze dry process. Lyophilization was then completed as described in the previous process description.

Example 2d

Uni-Directional Freezing (Log Method)

Suspensions were loaded into long polymer or metal tubes using larger amounts (5-50 ml) of material. These materials once frozen and dried produced long logs of either axially or radially configured cell culture scaffolds that were later sliced into thin discs of useable material for insertion into individual cell culture containers or cell culture wells. Scaffolds were cut into discs using a razor blade. Slices of matrix can be held in place by a snap ring. The process of axial or radial freezing using the log method is similar to those sample processes described above, but is done in tubes with conductive bottoms for axial freezing or tubes with conductive sides for radial freezing. Lyophilization is then completed as described in the previous process description.

Example 3

Cell Culture

Scaffolds made by any of the above methods were held in a TCT plate and sterilized using a UV lamp (366 nm) for 1 hour before culture substrates were incubated with media for 0.5 hour. Then, a cell solution was added onto the scaffold directly after removing the pre-incubation media. The cell solution contained HepG2/C3A cells obtained from American Type Culture Collection (ATCC). Frozen cell were thawed and cultured in Eagle's Minimum Essential Medium (EMEM) on Corning CellBind surface and kept at incubator under 37° C. with 5% $CO_2$. Cells were plated onto substrates in EMEM containing 10% FBS and 1% antibiotic and were grown at 37° C. with 5% $CO_2$.

Example 4

Characterization of Cell Growth and Function

Figure 10:
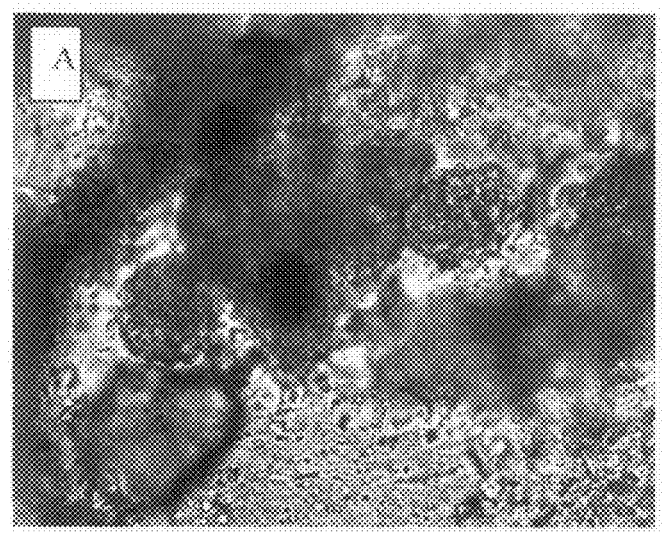
FIGS. 10A, B and C are a series of photomicrographs showing bright field, live staining and dead staining of cells growing on embodiments of the matrix of the present invention.
Figure 10:
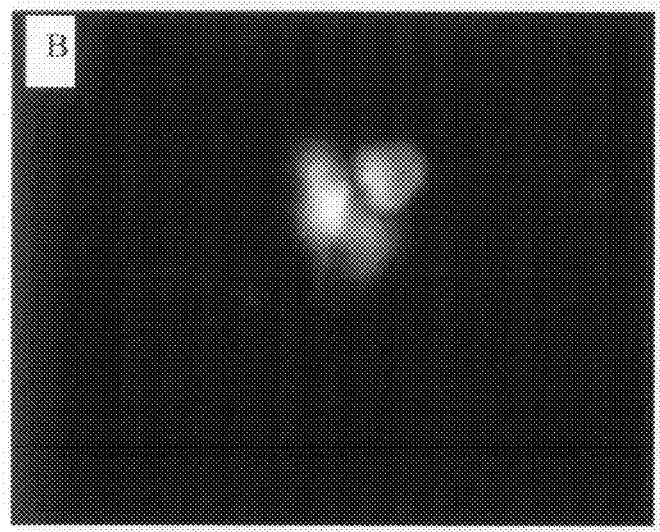
Figure 10:
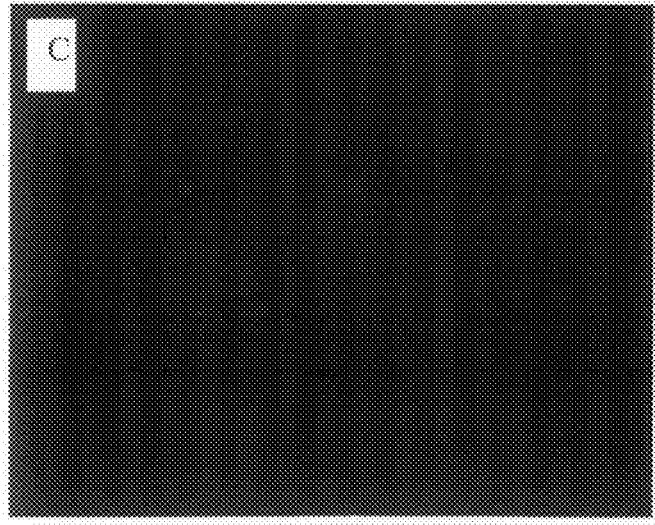

FIGS. 10A, 10B and 10C are a series of photomicrographs showing bright field, live staining and dead staining of cells growing on embodiments of the matrix of the present invention. FIG. 10A is a bright field photomicrograph image showing cell morphology of hepatocytes growing on a locust bean gum scaffold embodiment of the present invention. Due to the three dimensional nature of the material, imaging can be difficult. However, from the bright filed image of FIG. 10A, the spheroidal morphology of cells growing on the locust bean gum scaffold can be observed. Modified fluorescence microscopy images are shown in FIGS. 10B and 10C. FIG. 10B shows live cells and FIG. 10C shows dead cells. These images were taken after the scaffold was treated with a LIVE/DEAD stain Live/Dead staining of HepG2/C3A cells 9 days after being cultured on the scaffold. The cells were stained with a Live/Dead staining reagent kit (live/dead viability/cytotoxicity kit purchased from Invitrogen—catalog number L-3224) and used according to the supplied protocols, where live cells are shown by green and dead by red, and the images were modified to black and white images for the purposes of publication.

Figure 11:
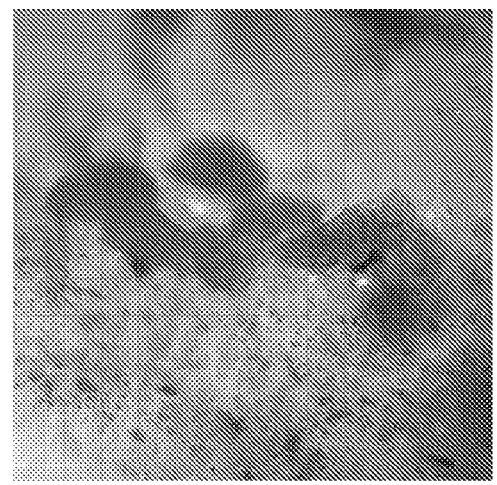
FIG. 11 is a bright field photomicrograph showing hepatocytes having spheroid morphology growing on an embodiment of the matrix of the present invention.

FIG. 11 is a bright field photomicrograph image taken by confocal microscopy showing cell morphology of hepatocytes growing on an embodiment of the matrix of the present invention. The cultured hepatocyte cells show spheroidal morphology.

Albumin production, an indication of the viability of hepatocyte cells in culture was measured for cells grown on a locust bean gum three dimensional porous matrix (LBG matrix) of the present invention and, for comparison, on a Matrigel™ surface, obtained from Becton Dickenson and prepared according to the insert instructions.

Figure 12:
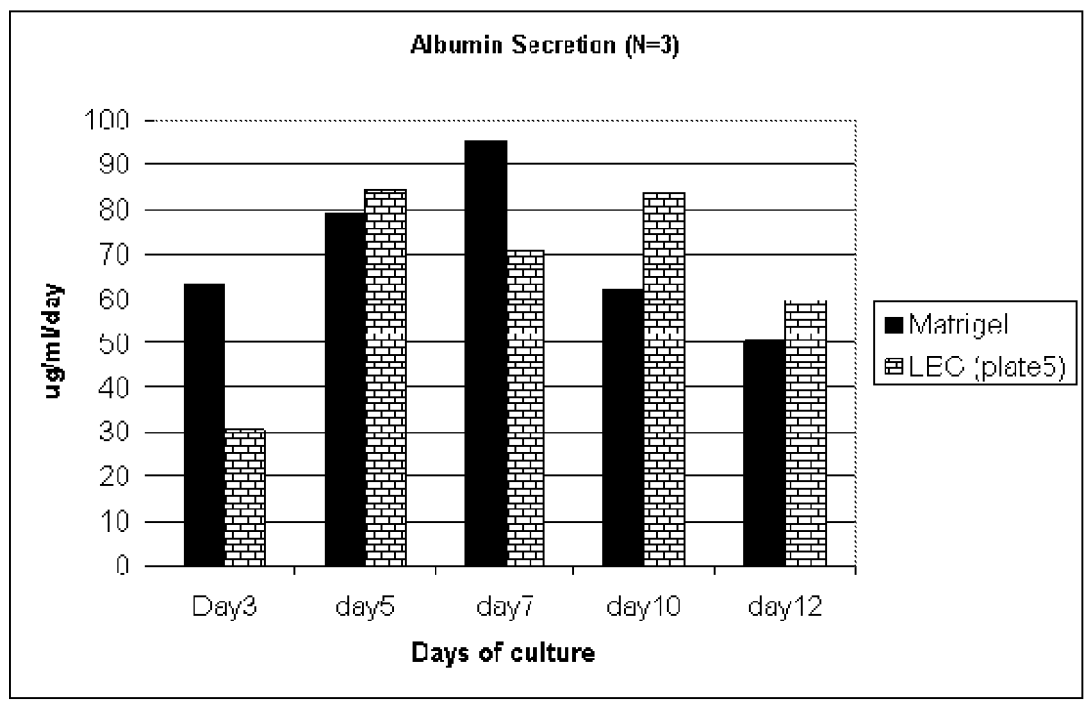
FIG. 12 is a chart illustrating albumin product of cells growing on an embodiment of the matrix of the present invention compared to albumin production of cells growing on Matrigel®.

FIG. 12 is a chart illustrating albumin product of cells growing on an embodiment of the matrix of the present invention compared to albumin production of cells growing on Matrigel®. The albumin amounts are relatively for both Matrigel™ and the LBG matrix (>60 μg/ml/day) there seems to be a lowering of the albumin with time (>day 7). Some gels break down during culture leading to removal of some material, including cells during culture. FIG. 12 shows that this effect is more marked in the Matrigel™ cultured cells than in the LBG matrix cultured cells. In the case of the LBG matrix, cells grow inside the substrate. Lowering of albumin could be due to difficulties in removing the media sample from a porous scaffold.

The invention and its embodiments being thus described, it would be obvious that the same may be varied in many ways by one of ordinary skill in the art having had the benefit of the present disclosure. Such variations are not regarded as a departure from the spirit and scope of the invention, and such modifications as would be obvious to one skilled in the art are intended to be included within the scope of the following claims and their legal equivalents.

What is claimed is:

1. A method of making a three dimensional cell culture matrix having directional porous structure comprising:
   a. providing a solution comprising locust bean gum;
   b. introducing the solution into a container;
   c. providing a heat sink, wherein the heat sink has substantially greater thermal conductivity from the container and wherein the heat sink is a portion of the container or a separate heat sink structure inside the container; and
   d. freezing the solution in the container to form the three dimensional cell culture matrix having directional porous structure, wherein the directional porous structure comprises a plurality of pores having a common orientation relative to the location of the heat sink.

2. The method of claim 1 wherein the solution further comprises at least one compound selected from the group consisting of guar gum, cassia gum, tara gum, mesquite gum, and fenugreek gum.

3. The method of claim 1 wherein the method further comprises culturing cells on the cell culture matrix.

4. The method of claim 3 wherein the cells comprise hepatocytes.

5. The method of claim 1 wherein the matrix further comprises a biologically active compound.

6. The method of claim 5 wherein the biologically active compound comprises amino acids, peptide, polypeptides, proteins, carbohydrates, lipids, polysaccharides, nucleic acids, nucleotides, polynucleotides, glycoproteins, lipoproteins, glycolipids, glycosaminoglycans, proteoglycans, growth factors, differentiation factors, hormones, nurotransmitters, pheromones, chalones, prostaglandins, immunoglobins, monokines, cytokines, humectants, fibrous proteins, or adhesion/deadhesion compounds.

7. The method of claim 1 wherein the container comprises labware.

* * * * *